United States Patent
Unsworth et al.

[11] Patent Number: 5,904,657
[45] Date of Patent: May 18, 1999

[54] SYSTEM FOR GUIDING DEVICES IN BODY LUMENS

[76] Inventors: John D. Unsworth, 365 Lodor St., Ancaster Ontario, Canada, L9G 2Z5; Thomas C Waram, 207 Charleton Ave. W., Hamilton On, Canada, L8P 2E3; Allan G Adelman, 100 Wychwood Park, Toronto On, Canada, M5G 2V5

[21] Appl. No.: 08/806,793

[22] Filed: Feb. 26, 1997

[51] Int. Cl.⁶ ........................................................ A61B 5/00
[52] U.S. Cl. .......................... 600/585; 604/281; 600/434
[58] Field of Search .................................. 600/434, 585; 604/95, 96, 280, 281; 606/1, 7, 15, 16, 17

[56] References Cited

U.S. PATENT DOCUMENTS

| | | |
|---|---|---|
| 3,773,034 | 11/1973 | Burns . |
| 4,033,331 | 7/1977 | Guss . |
| 4,248,234 | 2/1981 | Assenza . |
| 4,498,473 | 2/1985 | Gereg . |
| 4,573,470 | 3/1986 | Samson . |
| 4,582,181 | 4/1986 | Samson . |
| 4,586,923 | 5/1986 | Gould . |
| 4,616,652 | 10/1986 | Simpson . |
| 4,685,473 | 8/1987 | Karcher . |
| 4,822,345 | 4/1989 | Danforth . |
| 5,090,956 | 2/1992 | McCoy ................................ 600/585 |
| 5,123,421 | 6/1992 | Sinofsky . |
| 5,147,370 | 9/1992 | McNamara . |
| 5,163,935 | 11/1992 | Black et al. ........................ 606/17 |
| 5,169,395 | 12/1992 | Narciso, Jr. ........................ 606/7 |
| 5,207,229 | 5/1993 | Winters ............................. 600/585 |
| 5,211,183 | 5/1993 | Wilson .............................. 600/585 |
| 5,238,005 | 8/1993 | Imran . |
| 5,334,168 | 8/1994 | Hemmer ............................ 604/281 |
| 5,345,937 | 9/1994 | Middleman et al. ............... 600/585 |
| 5,370,649 | 12/1994 | Gardetto et al. ................... 606/7 |
| 5,382,238 | 1/1995 | Abrahamson . |
| 5,395,330 | 3/1995 | Mareadis . |
| 5,439,447 | 8/1995 | Miraki . |
| 5,445,625 | 8/1995 | Voda . |
| 5,476,100 | 12/1995 | Galel . |
| 5,487,740 | 1/1996 | Sulek et al. ....................... 606/17 |
| 5,498,239 | 3/1996 | Galel ................................. 604/95 |
| 5,531,685 | 7/1996 | Hemmer ............................ 604/95 |
| 5,569,197 | 10/1996 | Helmus et al. .................... 604/96 |
| 5,605,162 | 2/1997 | Mirzaee ............................. 600/585 |
| 5,637,089 | 6/1997 | Abrams et al. ................... 604/95 |
| 5,666,968 | 9/1997 | Imran et al. ...................... 600/585 |
| 5,690,971 | 11/1997 | McGurk et al. .................. 600/585 |
| 5,730,741 | 3/1998 | Horzewski et al. .............. 600/585 |
| 5,807,389 | 9/1998 | Gardetto et al. ................. 606/17 |
| 5,827,268 | 10/1998 | Laufer ............................... 606/28 |

FOREIGN PATENT DOCUMENTS 0 363 661  4/1990  European Pat. Off. .

*Primary Examiner*—Max Hindenburg
*Assistant Examiner*—Charles Marmor, II

[57] ABSTRACT

A system for guiding devices or materials into body lumens includes a guidewire made of a shape memory alloy (SMA) or other shape memory material and having a lumen; an energy guide, preferably an optical fiber, received in the lumen; and a catheter or device slidably attached to the guidewire. The guidewire has a memorized shape and is in a martensitic (deformable) state during insertion into the body lumen. During or after insertion of the guidewire into the body lumen, the energy guide produces localized heating of the inner surface of the distal end of the guidewire, to cause the guidewire to at least partially recover its memorized shape, thereby selectively changing the shape, radii of curves, and rigidity of part or all of the guidewire. This selective shaping of the guidewire reduces fouling and facilitates delivery of devices along the guidewire.

20 Claims, 13 Drawing Sheets

Fig. 1A
Fig. 1B
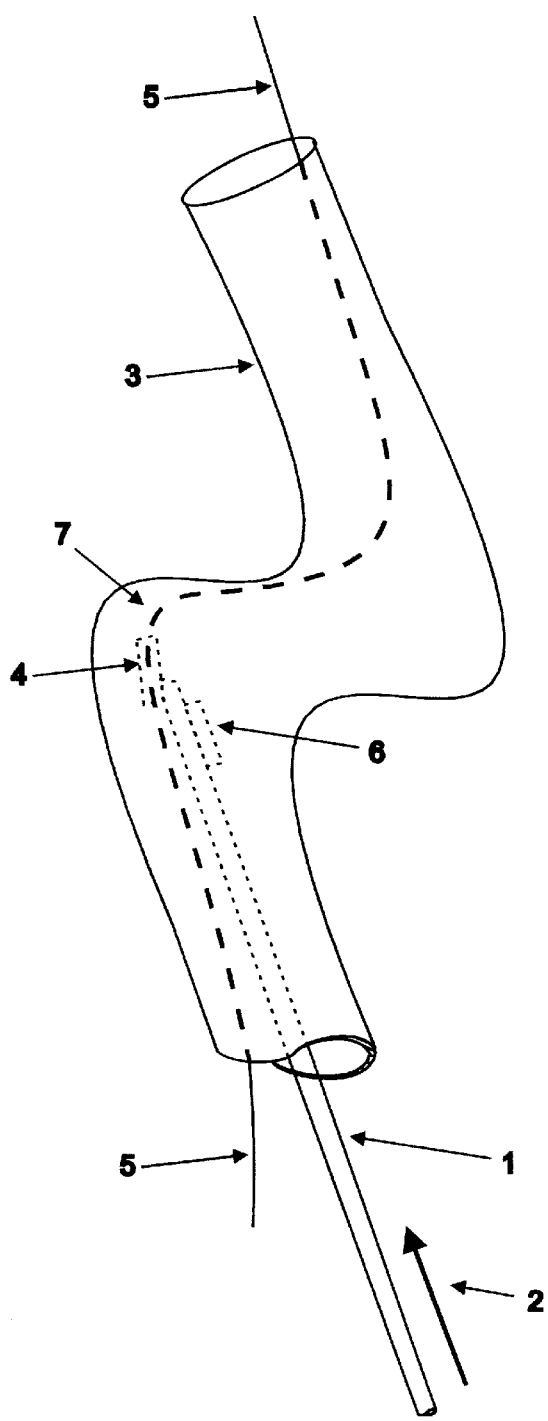
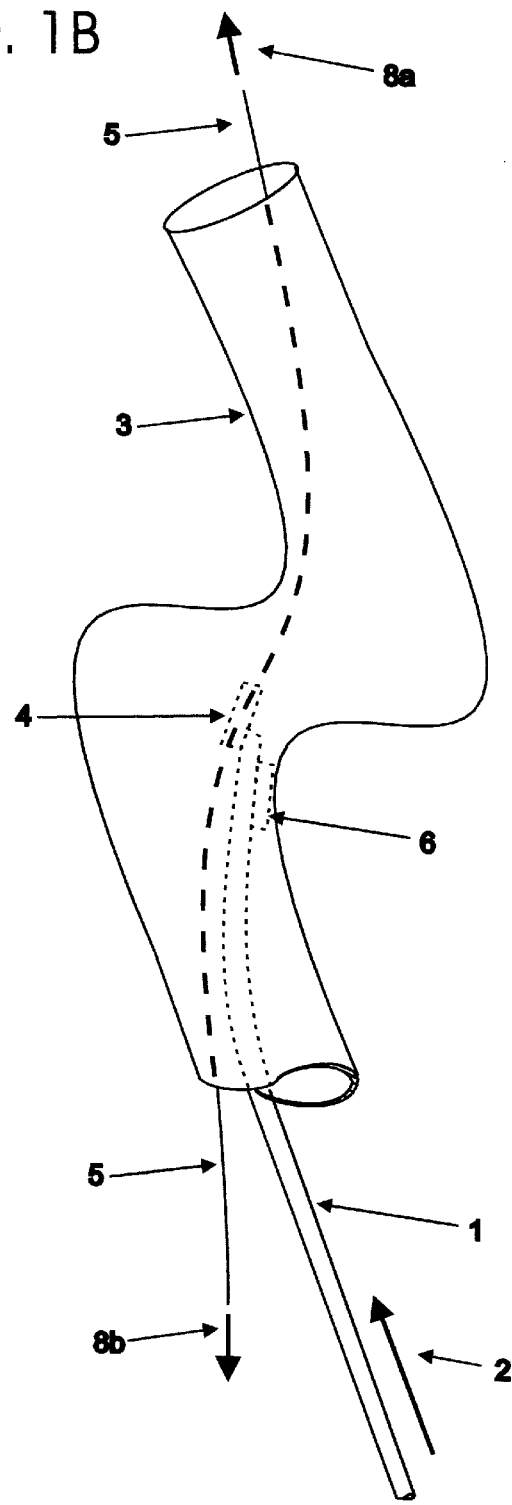

Fig. 2A
Fig. 2B
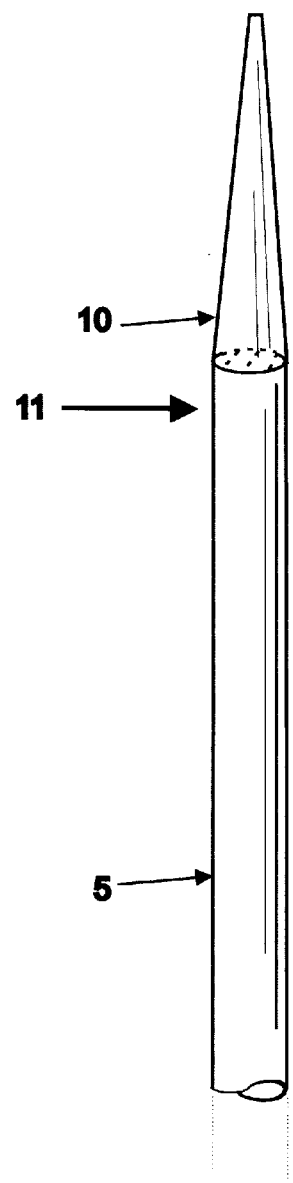
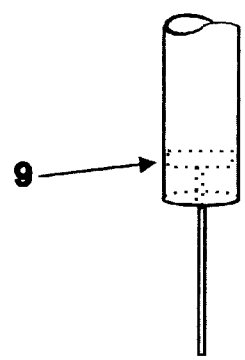
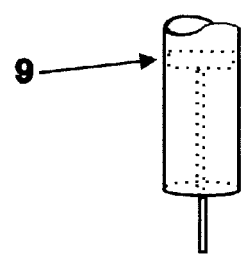

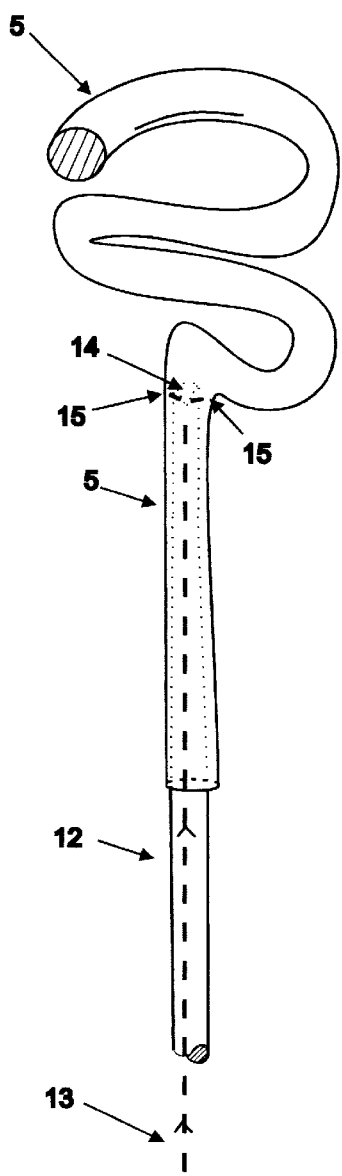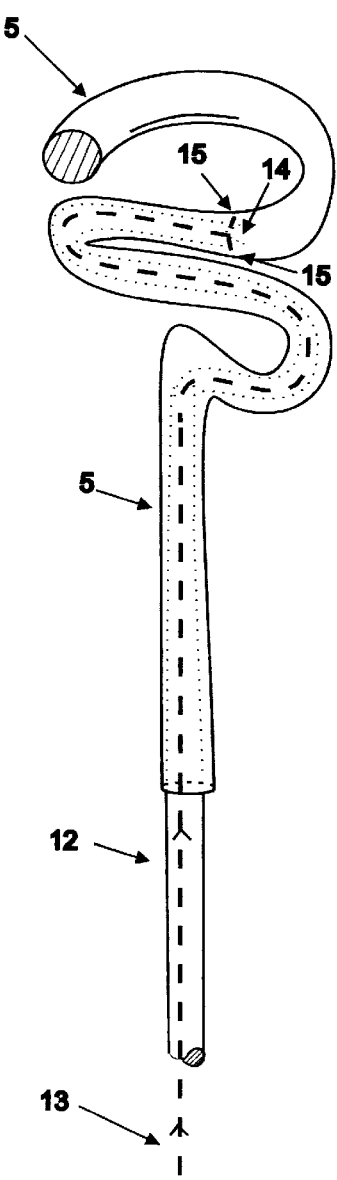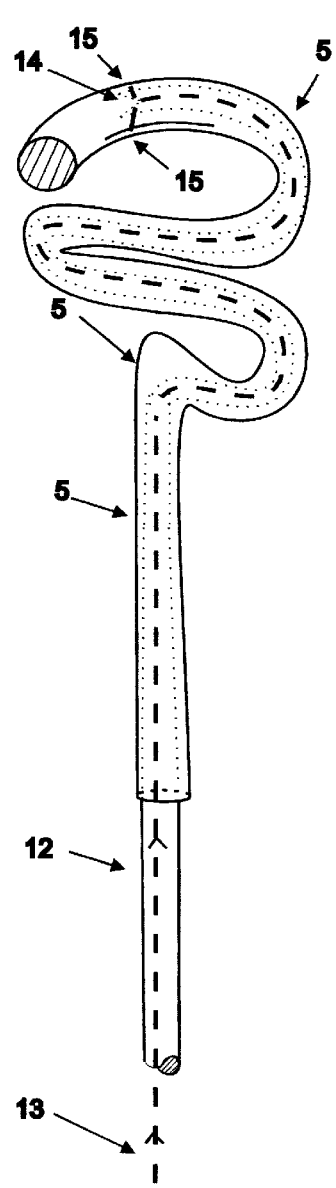

Fig. 7A
Fig. 7B
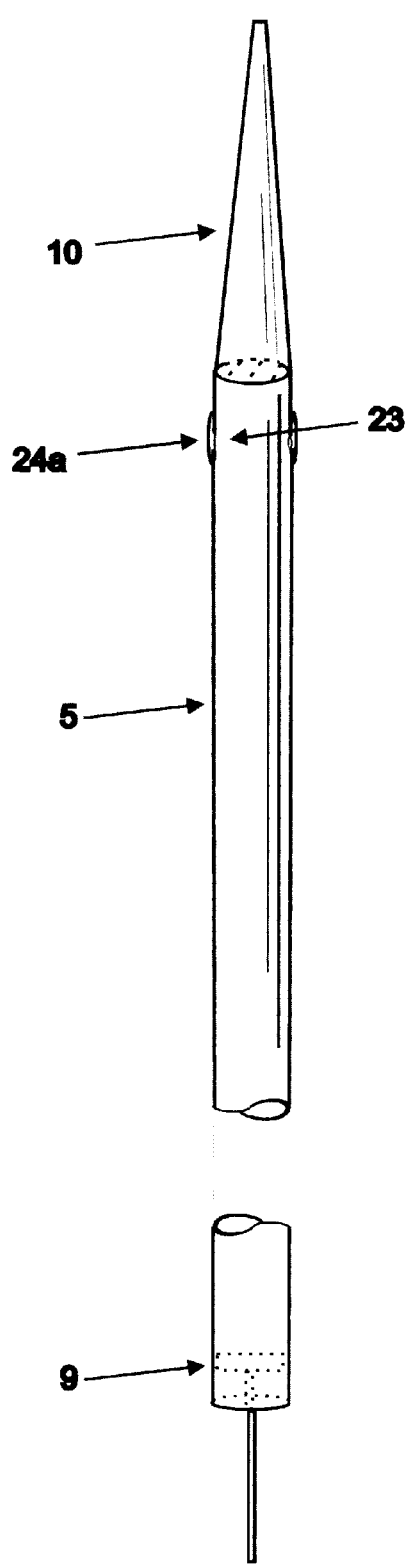
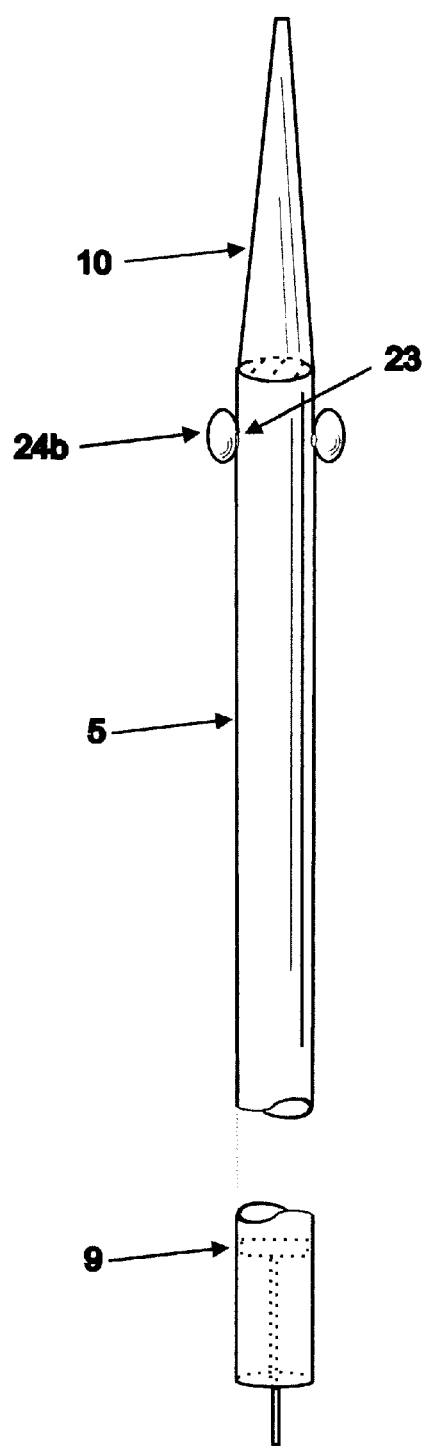

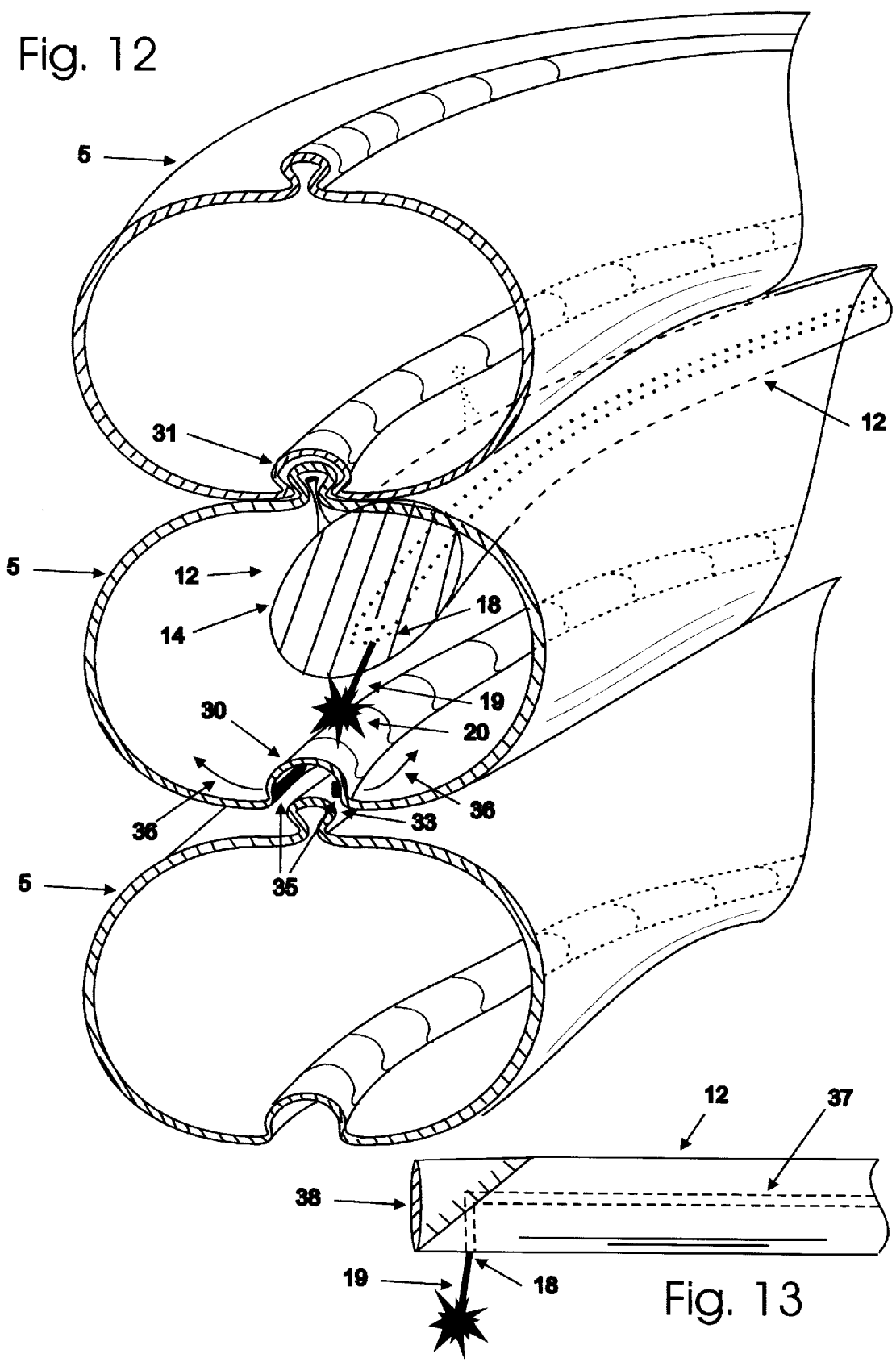

SYSTEM FOR GUIDING DEVICES IN BODY LUMENS

FIELD OF THE INVENTION

Many operations require the feeding of devices through lumens of hollow body structures. For example, percutaneous transluminal coronary angioplasty (PTCA) operations require the feeding of a balloon and sometimes stent into the cardiovascular system via the femoral artery under local anesthesia. Danforth in U.S. Pat. No. 4,822,345 describes the typical angioplasty procedure, paraphrased, as follows. In a routine angioplasty procedure using conventional catheters, a preshaped semi-rigid guiding catheter is introduced into a peripheral artery, advanced over a guidewire along the course of the aorta and subsequently engaged within the appropriate coronary ostium. Once engaged, a second catheter (an angioplasty balloon dilation catheter), equipped with a balloon at its distal aspect and a flexible steerable guidewire, is introduced within the guiding catheter and advanced to within its distal aspect. The guidewire is then advanced within the lumen of the diseased vessel and manipulated across the region of stenosis. By rotating the guidewire, which contains a slight bend, the operator can control the course of the wire and select the appropriate lumen. Once the guidewire is positioned across the region of stenosis, the operator advances the dilation balloon over the guidewire and positions it across the stenotic lesion. The angioplasty is then accomplished by inflating the balloon to 6 to 10 atmospheres of pressure. Usually three to four dilations are required for each region of stenosis, with the duration of each dilation varying between 30 to 90 seconds, depending upon anatomic considerations and operator preference. Following the final dilation, the guidewire and angioplasty balloon are withdrawn leaving the guiding catheter in place, or if a stent is to be placed at the region of stenosis, the first balloon catheter is removed, and a second balloon catheter with stent covering it are introduced to the region of stenosis and the balloon is expanded, thus deploying the stent. If the latter procedure is followed, the second balloon catheter and guide wire are then removed leaving the stent in place. Coronary angiography may then be performed to evaluate the appearance of the vessel following the procedure and to determine the severity of any residual stenosis. [end of paraphrased reference]

The balloon catheter that passes over the guidewire can be configured in the so-called "monorail" configuration which is well known in the art. Such monorail catheters generally have a comparatively short distal monorail portion of the catheter slidably received over a guidewire. This distal portion includes an expansible dilation balloon. Other than the comparatively short distal portion of the guidewire, received within the catheter, the remainder of the guidewire of these monorail systems is exposed externally of the catheter. Other types of catheters have lumens along their entire length that slidably receive the guidewire, that is not exposed externally of the catheter.

These guidewires have a combination of physical characteristics that make them well suited to course, without fouling, through the lumen's often tortuous path. The most important characteristic is that they are relatively flexible and at the same time have a tendency to return by springing motion to their original line or generally straight shape.

It is this combination of physical characteristics plus their low sliding resistance that makes them suitable to act as a harbinger for the more bulky catheters and devices that they later guide. Once in place, these guidewires act as directing means for other devices that are connected to them, but are free to slide along them when pushed by some pushing means, such as a catheter. The difficulty with such methods is that the device that is being pushed along the guidewire is often not as flexible as the wire and is often obstructed by small radius bends in the lumen. This is usually caused by the fact that the distal end of the device, at a turn, under-turns and plows into the part of the bend having the larger radius, that is, the out-side of the bend. The constraints imposed on the proximate end of the device then overpower the redirecting means provided by the guide-wire on the distal end of the device. An analogy of the situation is a car turning a sharp corner. If the car's front wheels could not be steered, the car would likely plow into the outside of the turn; if on the other hand the front wheels could be steered, and in addition, the front wheels were powered to pull the car around the turn, the car would more likely negotiate the turn. Generally, when a device is pushed by a guidewire, the guidewire is pushed to the outside of the bend, distorting and reducing the radius of the bend of the guidewire, as illustrated on FIG. 1A. If a device is pulled along the wire, it pulls the device to the inside of the bend, increasing the radius of the bend. Ideally a device would be both pushed and pulled to keep the device in the center of the bend, or center of the lumen. What is needed therefore is a means of augmenting the redirecting means acting on the distal end of the device. A stiffer guiding wire, might seem to be the obvious solution, but this would cause difficulties of feeding the wire into the lumen and cause excessive damage to the cells lining the cavity into which the device is inserted.

It would be desirable to have a guiding means that would be flexible while inserted, to minimize damage to the endothelial cells, but allow the surgeon to increase the stiffness of the guidewire once in place to better act as a guide. It would also be desirable to have a guiding means that would pull devices as well as push them through body lumens. It would also be desirable to be able to put the guiding means under tension during the operation. This invention provides such means. Generally, this invention includes a means of increasing the radius of the bends in the guiding means.

Methods of stiffening catheters for various purposes has been described in the prior art. For example, the Samson patent, U.S. Pat. No. 5,382,238 describes a catheter that has one or more lumens into which wires of various stiffness can be inserted, thereby increasing the stiffness of the catheter. The purpose for which the catheter is stiffened is to assist in inserting the otherwise flacid catheter into body lumens. A similar approach for the same purpose is described in the Assenza patent, U.S. Pat. No. 4,248,234. In the Assenza patent, the stiffening means is provided by a lumen in the catheter that is pressurized which stiffens the otherwise limp catheter and makes possible its insertion into a body lumen by pushing action. As noted above, this approach is not appropriate where the body lumens are small or very tortuous, since the stiffening of the catheter in combination with the pushing action can cause damage to the cells lining the inside of the body lumen. For more tortuous body lumens, the use of a very flexible guidewire, with a small cross-sectional area causes much less damage and can be maneuvered through a vary tortuous path. As described above this guidewire can then guide the main catheter, which can remain relatively flexible, to the appropriate place in the body lumen, without causing excessive damage to the cells lining the body lumen. Unlike the devices described in these patents, the present invention stiffens the guidewire only when the guidewire is in place and is not again pushed thought the body lumen. By using a guidewire with controllable stiffness, and achieving the insertion of the catheter in three separate steps: insertion of flexible guidewire, increasing its stiffness and finally, insertion of the catheter over it or along it, much injury to the lining of the body lumen is obviated.

Several other patents have utilized increased pressure to stiffen or change the shape of the catheter. The Karcher patent, U.S. Pat. No. 4,685,473, pressurized bellows attached to the side of the catheter to bend the catheter in a radial direction opposite to the inflated bellows. Similarly the Danforth patent, U.S. Pat. No. 4,822,345 describes a "Judkins" type guiding catheter that has a pressurized distal end that maintains the radius of the guiding catheter or changes its shape in response to changes in pressure of lumens located in the distal end of the catheter. The Danforth patent is meant to stabilize and position the distal end of the guiding catheter in the aorta, perfectly coaxially with the a coronary ostium to permit the guiding of a balloon catheter and guidewire into the lumen of the selected coronary artery. The Burns patent, U.S. Pat. No. 3,773,034 describes a catheter with a steerable tip that bends in one or more directions in response to the application of various fluid pressures to lumens passing through the length of the catheter to a flexible tip.

Another method of stiffening or shaping the hollow guidewire after it has been placed in the body lumen is described by Unsworth and Waram in a copending patent application, Ser. No. 08/749661 filed on Nov. 15, 1996, which patent application is incorporated herein by specific reference. That patent describes a method of imparting virtually any shape on a shape memory alloy (SMA) tube, or a tube made of material having similar materials that exhibit shape recovery when heated to an appropriate temperature. That patent application describes a device comprised of a side-firing laser or electrical probe that selectively heats parts of the inside of a tube of SMA material. By shape setting the tube to the desired shape at high temperature, then deforming the tube after it has cooled below the temperature at which it completely or nearly completely changes into its martensitic phase, one can create many shapes by heating part or parts of the tube to the temperature at which the selected parts of the material is transformed into its austenitic phase, thus recovering parts of the shape set into the tube at high temperature. SMA becomes more rigid in addition to recovering its memorized shape where heated sufficiently to transform that part heated to its austenitic phase. That patent application did not however describe the use of the method to stiffen or shape a hollow guidewire for guiding catheters through tortuous body lumens, and did not describe methods to cool tubes from their austensitic phase to their martensitic phase to reduce the stiffness of the material and make possible the relatively large non-permanent deformation which is characteristic of the martensitic phase, which can be recovered upon subsequent heating.

The use of cuffs or balloons attached to the distal end of catheters is common to prevent the accidental retraction or rejection of the catheter. It is usual to inflate the cuff from an outside source of air or by pressurizing a saline solution using for example a piston pump similar to that used in angioplasty operations to inflate the balloon. Representative of the prior art in this field is a Weikl et al, U.S. Pat. No. 4,573,966 and Pierpont, U.S. Pat. No. 5,484,412. The prior art however does not disclose the use of a cuff on a guidewire for the purposes of tensioning the guidewire by pulling on the proximal end while the distal end is anchored to the inside of the body lumen, for the purposes of reducing the radius of the bends in the guidewire that traces the tortuous body lumens.

SUMMARY OF THE INVENTION

One embodiment of the invention is to use a wire that has one or more lumens running inside the wire, along the wire's longitudinal axis, rather than a solid wire, to act as the guiding means for other devices. The lumen of the hollow guidewire can be pressurized with a saline solution or some other suitable material using a simple piston compressor or similar pressurizing means attached to the proximal end of the said hollow wire. This compressing means can be similar to the devices that inflate angioplasty balloons. The purpose of increasing the pressure inside the hollow guidewire after the tube is inserted into the lumen of the body cavity is to increase the hollow guidewire's rigidity and to thereby straighten it. This increased rigidity not only maximizes the radius of bends by straightening the guidewire, but also resists the tendency of a device that is connected to a catheter and that is pushed along the hollow guidewire from distorting the smooth curve of the hollow guidewire as it follows the bend of the lumen of a body cavity. The increased rigidity then increases the redirecting forces acting on the distal end of the device being pushed along the hollow guidewire, and reduces the chances that the device, as it is pushed, will distort the hollow guidewire and create a turn of smaller radius.

Another embodiment of the invention is to use a hollow guidewire made of superelastic shape memory alloy (SMA) that has been given a shape setting heat treatment at elevated temperatures such that it is straight when it is predominantly austenitic. Many guidewires are made of superelastic material since they have good torqueability and are very flexible. A superelastic shape memory alloy is processed such that its austenitic finish temperature is always below the temperature at which the material will be used, in this case, approximately body temperature (37° C.). Thus in a low stress or stress-free condition, the material will exist in the austenite phase. As a superelastic guidewire bends, it reaches a critical bend radius at which stress induced martensite (SIM) forms from the predominately austenitic material matrix. This is because there is a critical stress level at which stress-induced martensite is formed from austenite. It is known that this stress level increases in a linear manner with temperature, for shape memory alloy materials, such as nitinol. It is the formation of stress induced martensite that allows the guidewires to be bent into small radiuses without incurring significant permanent plastic deformation. This is because when the bending forces are removed, the wire will return to its normal straight shape, due to the fact that the stress induced martensite will revert to austenite in a reversible manner, such that all or almost all of the stress-induced martensitic deformation disappears. If the guidewire was made of a tube, as is the case with the preferred embodiments of this invention, and the hollow guidewire was put in place in the body lumen, those parts of the tube that are bent beyond the critical bend radius will have undergone a change from austenite to stress-induced martensite, to varying degrees, depending on the radius of the bend: the smaller the radius of the bend the greater the amount of the material contained in the tube at that point would be transformed to stress-induced martensite. If one could then heat those parts of the tube that have become partly or wholly stress-induced martensite to a higher temperature, those parts would undergo a partial or complete reversion to austenite and become stiffer and straighter since the temperature rise will cause a thermodynamic shift in the equilibrium amounts of austenite and martensite, in favour of more austenite. This stiffening and straightening would result in larger radius turns and would make the guide more effective in guiding catheters that are designed to slide along the guidewire. It is important to note that those parts of the hollow guidewire that are bent most, that is, have the smallest radius turns, and therefore a high stress-induced martensite content, will generate more force when they endeavor to return to their memorized shape when heated sufficiently to cause the full or partial reversion from martensite to austenite. This suggests that the entire hollow guidewire could be heated and only those parts with small radius turns would show large relative increases in stiffness with a concomitant propensity to straighten; these parts being the only parts that one would wish to stiffen and straighten. This heating could be achieved by a number of means including hot saline solution pumped into the lumen of the hollow guidewire. The difficulty with this method is that in the case of the body being a human body, the temperature of heating the entire tube might cause cell damage to the body lumen into which the guidewire is placed.

Heating of the hollow guidewire in specific locations as taught by Unsworth and Waram in a copending patent application, Ser. No. 08/749661 filed on Nov. 15, 1996 is much preferred, as little heat is transferred to the surrounding tissue. Utilizing these methods, the hollow guidewire would receive in its lumen a device that would transfer energy to the inside of the hollow guidewire at specific locations. The patent application of Unsworth and Waram, Ser. No. 08/749661 filed on Nov. 15, 1996 describes many methods for effecting such an energy transfer and any and all of those could be adopted for the purposes of this invention. By way of example one preferred embodiment of the invention would be to utilize a side-firing optical fiber that would slide inside the lumen of the hollow guidewire. The optical fiber would transport photo-thermal energy from an external source, down through the optical fiber, to the distal end of the fiber. At the distal end of the fiber a redirecting means is attached or fabricated into the distal surface, that redirects the photo-thermal energy approximately normal to the longitudinal axis of the optical fiber and projects that energy onto the inner surface of the hollow guidewire, into which it is placed. Hot fluids can also be delivered to those parts selected, by using a tube with a small side-firing orifice, that projects the hot fluid onto the inside surface of the tube.

Utilizing the same method as taught by Unsworth and Waram in a copending patent application, Ser. No. 08/749661 filed on Nov. 15, 1996, in addition to stiffening and straightening the hollow guidewire made of superelastic material at specific places as described above, one could utilize a hollow guidewire made of shape memory SMA that has had a specific shape set into the tube at high temperatures. This shape might conform to the shape of a tight turn or compound turn in the body lumen into which it is fed. When this tube is then returned to its low temperature martensitic phase, it can be deformed into a shape suitable for inserting into the body lumen (usually this will be straight). Once in the body lumen, the hollow guidewire could then be heated to or above its austenite finish temperature and it would then recover its memorized shape, that is for example a tight turn or compound turn. This heating could be effected by many means including those methods taught by Unsworth and Waram in a copending patent application, Ser. No. 08/749661 filed on Nov. 15, 1996. Unsworth and Waram also taught in said patent application methods of heating specific locations within the tube to generate many different shapes from tubes that had undergone the same shape setting and deformation regimes. All these methods could be utilized to shape the hollow guidewire after it has been inserted into the body lumen so as to optimize its shape for the purpose of guiding catheters that are slid along the hollow guidewire's length.

One difficulty of using SMA that is not superelastic, that is that has shape memory effect instead, for this application is that in the martensitic phase the material is unable to sustain much elastic or superelastic deformation, but instead undergoes a crystallographic detwinning process at relatively low stress levels in which relatively large amounts of reversible deformation can be accumulated (this deformation can subsequently be reversed by heating above the austenite finish temperature). In most cases this makes it unsuitable for insertion into a body lumen that is tortuous. One preferred embodiment of the invention that overcomes this difficulty is to have a tube within a tube to comprise the hollow guidewire. These tubes would be bound together by friction, contact forces, or other means so as to act as one element. One of the tubes could be manufactured so as to be superelastic within a temperature range that includes body temperature (37° C.) and the other made such that it exhibits the shape memory effect (SME), i.e., it would remain mostly in the martensitic phase at body temperature, and would undergo a phase transformation to austenite when heated to or above an austenite finish temperature greater than body temperature (37° C.). If the outer tube was superelastic and the inner tube was made to behave with the shape memory effect, one could shape the inner tube as taught by Unsworth and Waram in a copending patent application, Ser. No. 08/749661 filed on Nov. 15, 1996, but still retain the superelastic behavior that makes superelastic material ideal for insertion into tortuous body lumens, prior to transforming the inner tube into its memorized shape and rigid austenitic form. These tubes would have different temperatures at which they would undergo phase transformations. For example, the superelastic material would have a lower austenite finish temperature, somewhat below body temperature (37° C.) compared to that of the shape memory effect inner tube, that would have austenitic start and finish temperatures above body temperature. This would allow the inner tube to be shaped by the application of sufficient heat to change the phase of the inner tube from martensite to austenite, but leave largely unaffected the outer tube (some nominal increase in the stiffness of the outer tube may occur). In addition, several SMA tubes within tubes could be utilized, with different phase transformation temperatures, different thicknesses and different recovery forces. These arrangement could result in a myriad of different shapes depending upon the heating regime, that is the temperature, time of heating etc. Also, some tubes might have holes that would allow outer tubes to be heated without heating the inner tubes at certain locations.

A further method of controlling the stiffness and the shape of the composite tube involves a mechanical state analogous to pressurizing of the inside of the tube. For example while the two tubes are in their martensitic state, the outside tube can be stretched radially (that is, the average tube diameter is enlarged) or longitudinally, or both or neither; at the same time the inside tube can be shrunk radially or longitudinally, or both or neither (obviously either the outside tube must be stretched or the inside tube must be shrunk in at least one direction). The inside tube would then be inserted into the lumen of the outside tube, and a press-fit would be facilitated by the springback that results from the limited elastic response of the tubes while in their martensitic phase. When one or both of the tubes are then transformed into their austenitic phase, the composite tube (as opposed to the single tubes) will stiffen due to an induced longitudinal tension in one of the tubes in combination with longitudinal compression in the other tube. Thus the stiffness of the tube can be enhanced by this additional technique, alone or in combination with other methods, including the other methods described herein. Methods for heating the tube or tubes to their austenitic state include using a side-firing laser as describes above. This system can also be comprised of a combination of a shape memory effect SMA tube and a superelastic tube. In this case the shape memory effect SMA tube would put the superelastic tube in compression or tension when it is transformed into its austenitic phase. As can readily be seen, this method of imparting stiffness on a composite member, is an example of a more general method that is particularly convenient for tubular sections, secondly, that the composite system can be comprised of different materials having different physical properties, including different resonant frequencies and thirdly, that this method can be achieved by various means that do not include resort to the use of memory metals. The general method is simply inserting a tube within the lumen of another tube, with their longitudinal axes parallel, and then bonding them together by friction, adhesive means or other means, so that when the tubes reach their equilibrium state at working temperature, the tubes are either in compression or tension, and the compression and tension are maintained by the opposite force of the other tube to which it is bound. An example of the third case is a method whereby, while the two tubes are separate, the composite tubular section is fabricated by heating the outside tube, causing it to expand, while at the same time cooling the inside tube, causing it to shrink. They would then be press fit while still in that condition, and perhaps while continuing to heat and cool the respective tubes, so that one tube is inside the lumen of the other tube and their mating surfaces are in intimate contact. When the composite tube's temperature returns to ambient, the tubular composite section then exhibits increased stiffness. By applying these methods the composite tube can be made stiffer, while at the same time imparting other physical properties, for example: reducing the tendency of the composite tube to expand or contract during heating and cooling, and altering the tubes resonant frequency. The choice of materials for each tube will also affect the characteristics of the composite section. While replacing the inner most tube with a solid rod, would impart similar properties to the assembly, in the case where shape memory metals or superelastic materials are used, the assembly would necessarily be heated from the exterior of the assembly by means well known to the art. Such a composite tubes or composite rods made by such methods could be used for such diverse uses as guide wires, boiler tubes, propeller shafts, bearings, journals, gun barrels, masts or organ pipes; in fact, any use that requires a stiff member.

Cooling of the inside of the shape memory effect SMA tube could also be utilized to change its shape and reduce its stiffness where required. This cooling would cool a patch of the inside of the tube below that temperature at which the material changes its phase from austenite to martensite (that is, the martensite finish temperature). By analogy to the methods taught by Unsworth and Waram in a copending patent application, Ser. No. 08/749661 filed on Nov. 15, 1996, a delivery tube containing a fluid cooling material could be inserted into the lumen of the shape memory effect SMA tube in the same way in which the optical fiber is inserted into the shape memory effect SMA tube. The end of the delivery tube could have an orifice that would spray patterns of various shapes on the inside surface of the shape memory effect SMA tube. This cooling could be done in combination with heating by other means at different places, or the same places on the inside of the shape memory effect SMA tube to change the shape and rigidity of the shape memory effect SMA tube at will. In addition fluid hot materials could be directed down the said delivery tube to provide heating.

Another embodiment of the invention is to use a hollow guidewire that includes an inflatable and deflatable balloon or number of balloons near its distal end. The purpose of including these inflatable and deflatable balloons is to anchor the distal end of the hollow guidewire on the interior wall of the lumen into which the guide is fed. Balloons travel along the guidewire very easily and do not often foul on their way through tight bends. This feature makes them useful to provide such anchoring means. The balloons can have spaces between them so as to allow the blood to continue to flow, even when they are inflated, but need not have such spaces. The balloons are deflated until the hollow guidewire is in the desired position in the lumen of the body cavity. The balloons are then inflated, and press against the inside of the walls of the lumen and, by friction, prevent the balloon and hollow guidewire to which it is attached, from moving along the longitudinal axis of the lumen. The balloons are inflated and deflated by increasing and decreasing the pressure inside of the hollow guidewire by the same means described above in the first preferred embodiment. Once the distal end of the hollow guidewire is thus anchored, the proximal end of the hollow guidewire can be slightly withdrawn, thereby increasing the radius of the bends of the hollow guidewire as it courses around the bends of the lumen. By thus tensioning the hollow guidewire, the hollow guidewire is also less likely to be distorted from its smooth curve into a smaller radius curve by the distal end of the device being pushed along the hollow guidewire as described above. Also since the hollow guidewire is pressurized while the balloons are inflated, it will become more rigid and increase the forces acting to redirect the distal end of the device as described above. In the case of an angioplasty procedure, to minimize damage to the lumen wall, the balloon can be inflated in the lesion as a separate procedure or as the step of expanding the vessel wall. If the balloon is expanded to expand the vessel wall, it will first be expanded at less pressure to provide an anchor so the device (balloon and stent) can be positioned just proximal to the lesion site using a separate catheter, that has been advanced and guided by the hollow guidewire. The hollow guidewire balloon can then be fully expanded to expand the diameter of the vessel wall. The balloon attached to the hollow guidewire can then be deflated and pushed with the hollow guidewire beyond the point of lesion and the device (another balloon and stent) can be moved the short distance to the lesion site to complete the procedure. When the procedure is complete, the balloon catheter and hollow guidewire and attached device are removed from the body lumen.

Another embodiment of the invention is to place a loop, slider or ring or passageway though the guidewire, near the distal end of the hollow or solid guidewire, through which a messenger wire is fed. One end of the messenger wire can then be attached or detachably attached to the device that is pushed along the guidewire or attached to the distal end of the catheter that pushes the said device; the other end of the messenger wire being pulled by the operator to augment the forces acting on the distal end of the device. This pulling action effectively increases the radius of the curved sections of the guidewire as it follows the curves of the lumen. This pulling action is usually applied in concert with the device being pushed on the proximal end with a catheter or tube that travels along the said hollow guidewire. In most cases, since the pulling forces are small, the hollow guidewire will be sufficiently stiff to transfer the pulling force to the device being pulled along the hollow guidewire, without buckling the hollow guidewire between the device being pulled and the location of the said loop or ring. This is especially likely if a hollow guidewire is used and the hollow guidewire is pressurized as described above and is therefore more rigid.

In another preferred embodiment of the invention instead of a loop or ring being attached near the distal end of the hollow guidewire, as described in the immediately preceding preferred embodiment. The hollow guidewire can contain an aperture through which the messenger wire can pass and then pass down through the lumen of the hollow guidewire and out of the hollow guidewire at a place that is convenient so the operator can pull the messenger wire as desired. This reduces the amount of messenger wire that comes in contact with the walls of the body lumen in which the hollow guidewire courses. If an aperture is used, rather than the ring or loop, a pressure seal at the aperture is required to maintain the desired pressure inside the hollow guidewire, if the tube is pressurized.

Another preferred embodiment of the invention is to locate anchoring balloons described above near the said loop or ring, or the said aperture. This avoids the possibility that when the messenger wire is pulled by the surgeon, the hollow guidewire will buckle between the loop, ring or aperture and the point at which the messenger wire is connected to the distal end of the device or the catheter that pushes the device. As in the previous preferred embodiments, the balloons would be inflated by increasing the pressure inside the hollow guidewire after the hollow guidewire is properly located inside the body lumen. The operator could also put tension on the guidewire by pulling the guidewire as described above in combination with the operator pulling the messenger wire to enlarge the radius of the guidewire turns, as described above. The balloons could later be deflated by reducing the pressure inside the said hollow guidewire and the hollow guidewire could then be withdrawn from the lumen of the body cavity. As mentioned above the balloons can be expanded at the site of lesion to minimize damage to the vessel wall. Once the device is drawn to approximately this point, the balloons can then be deflated and the catheter delivering the device can be pushed the extra few inches into position at the lesion site, the balloons and hollow guidewire being advanced to a site more distal in the lumen.

Another embodiment of the invention is to cause the distal end of the hollow guidewire that is made of shape memory alloy to reform into a coil or other suitable shape in response to being heated above the austenitic finish temperature. This coil or other shape would be of such dimensions that it would press against the inside walls of the body lumen and thereby act in the same way as the balloon or cuff described in the immediately preceding paragraph. When desired the coiled shaped distal end of the hollow guidewire could be returned to its former shape by pumping a cold saline solution into the lumen of the hollow guidewire. The said saline solution would need to be sufficiently cool so that it would return the distal end of the hollow guidewire to its martensitic phase and thereby allow the coil or other shape to be drawn into a catheter that would straighten out the coil and permit its removal from the body lumen. Another means of returning the coiled shape to its former shape is to couple a springing element to the distal end of the hollow guidewire. This springing element would normally take the form a sheaf covering the part of the hollow guidewire that would form into a coil. Its normal shape would be approximately straight or that shape that would be most convenient to effect the removal of the guidewire. When the distal end of the said guidewire is then heated to above its austenitic finish temperature and the memorized shape is recovered, the springing element is sprung, but not so much that it materially effects the recovered shape. When the coil is later cooled however below the martensitic start temperature and the coil is compliant, the force of the spring is sufficiently strong to deform the compliant coil shape into a straight shape in conformity to the shape of the springing element.

Another embodiment of the invention is a method of transforming the coil shaped distal end of the hollow guidewire, made of shape memory alloy, into a larger rigid hollow tube. This is done in two steps. The first step involves forming the hollow guidewire into a coil by those methods taught by Unsworth and Waram in a copending patent application, Ser. No. 08/749661 filed on Nov. 15, 1996, in such a way that part of the hollow guidewire is not heated above its austenitic finish temperature and thus that part not heated does not recover its memorized shape. A sufficient amount of the said hollow tube is heated during the first step so that the general shape of the coil is recovered. The part of the tube that is not heated is a linear strip running parallel to the longitudinal axis of the hollow guidewire. The strip is coincident with a clincher type couple that forms part of the tube and is designed to recover its memorized shape when heated during the second step of the procedure, and when so recovered to grip a complementary couple located on the exterior of the next turn of the coil. By heating that part of the tube, from one end to the other, the coils of the tube will be zippered together to form a rigid tube. The coupling can have compliant seals that ensure a completely mated unit. In addition to serving in place of the anchoring balloons to hold the distal end of the hollow guidewire in place, the same device could be used for many purposes such as a stent, to reline the lumens of tubes or to form a spar in space. The coil can be unzipped by cooling the couple that was first heated in a similar manner. This is most conveniently effected by a combination optical fiber and cooling material delivery lumen that in contained within the optical fiber and that has a longitudinal axis that runs parallel to that of the optical fiber. The said delivery lumen has a redirecting means at approximately the distal end of the optical fiber that projects a spray onto the inside of the hollow guidewire and onto the said couple. Another means of zipping and unzipping surfaces is to use hooking fingers and hoops rather than the clincher type of couplings described immediately above. The hooking fingers are made shape memory alloy that form hooks when heated above their austenitic finish temperature, recovering their memorized shape of a hook. These hooking fingers are coupled to a springing element that pull the fingers straight when below their martensitic start temperature but are not strong enough to resist the hooking of the finger when the finger is heated above its austenitic finish temperature. The result is a smart type of hook and loop material that opens and closes in response to temperature change. If the temperature change proceeds along the material in a front, like a wave, the effect is that of a zipper. These motion of these hooking fingers can also be coordinated by the use of computer controlled peltier junctions to propel devices including guidewires along surfaces.

DRAWINGS

FIG. 1A is a perspective view of a section of a body lumen illustrating a typical compliant guidewire that is having its radius of curvature around a bend being reduced by a relatively stiff catheter being slid over it.

FIG. 1B is a perspective view of a section of a body lumen illustrating a hollow guidewire that is pressurized and or put under tension, resulting in the maintenance of larger radius turns of the guidewire, even when a relatively stiff catheter is slid over it.

FIG. 2A is a perspective view of a hollow guidewire illustrating the guidewire in its relatively compliant, low pressure mode being distorted from its normal straight shape by the application of a force, normal to its longitudinal axis.

FIG. 2B is a perspective view of a hollow guidewire illustrating the guidewire in its relatively rigid, high pressure mode resisting the application of the same force applied to the hollow guidewire illustrated in FIG. 2A above and retaining its normal straight shape.

FIG. 3A, 3B and 3C are perspective views of a hollow guidewire into which a side-firing optical fiber, that is delivering photo-thermal heating at its distal end, is being pushed, simultaneously causing the SMA tube to recover its memorized high temperature shape, and causing the hollow guidewire to become more rigid; sequentially from FIG. 3A to FIG. 3C.

Figure 5:
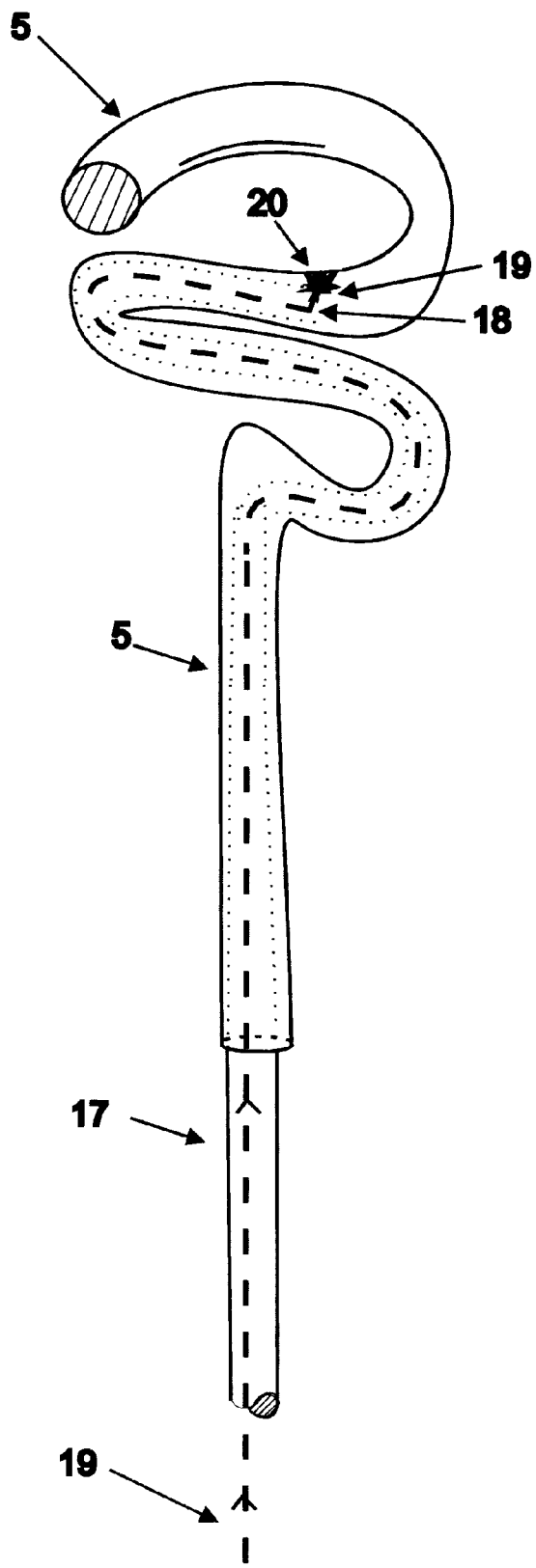

FIG. 5 is a perspective view of a SMA hollow guidewire into which a side-firing cooling delivery tube is extracting heat from the SMA tube on a defined patch on the inside of the tube to relax the memorized high temperature shape, and to cause that part of the tube so cooled to change its phase from austenite to martensite. FIG. 5 also illustrates a method for applying hot liquid material to the inside of a SMA hollow guidewire to recover a memorized high temperature shape by changing its phase from martensite to a austenite.

Figure 6A:
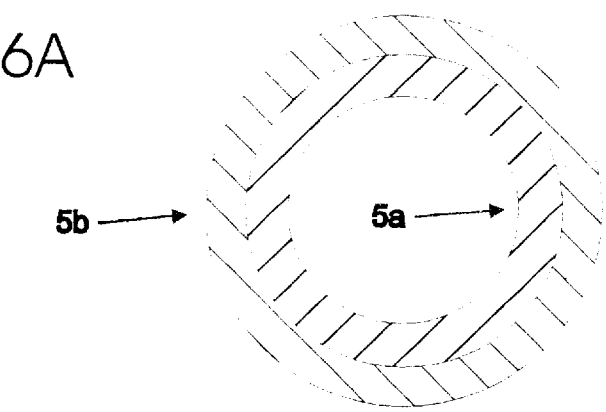
Figure 6B:
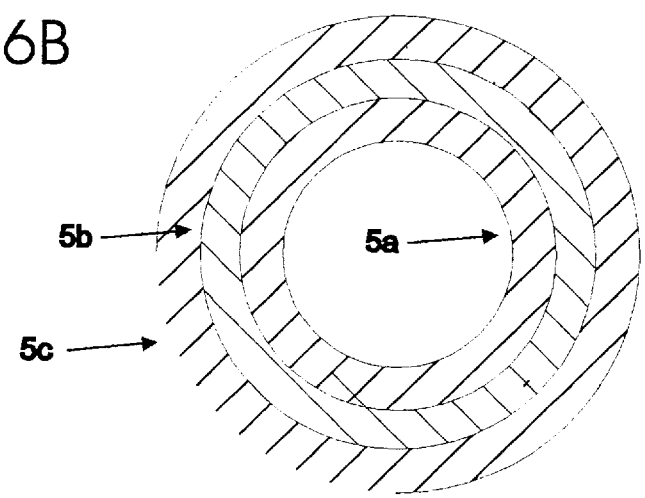
Figure 6C:
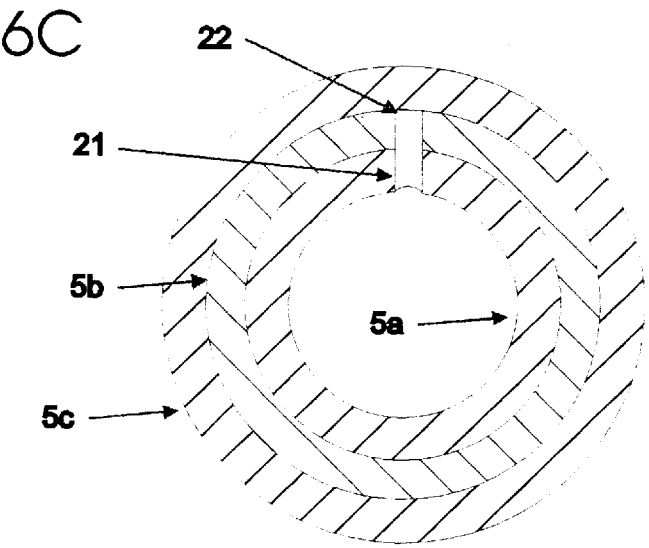

FIG. 6A, 6B, and 6C are cross-sectional views of a section of a hollow guidewire made of shape memory effect or superelastic tubing. FIG. 6A, illustrates a simple tube within a tube. FIG. 6B illustrates a three tube set and FIG. 6C illustrates a three tube set, where an access hole has made the outermost tube's inner surface accessible from the central lumen of the three tube set.

FIG. 7A is a perspective view of a hollow guidewire illustrating the guidewire in its low pressure mode with balloons attached in their deflated mode.

FIG. 7B is perspective view of a hollow guidewire illustrating the guidewire in its high pressure mode with balloons attached in their inflated mode.

Figure 8A:
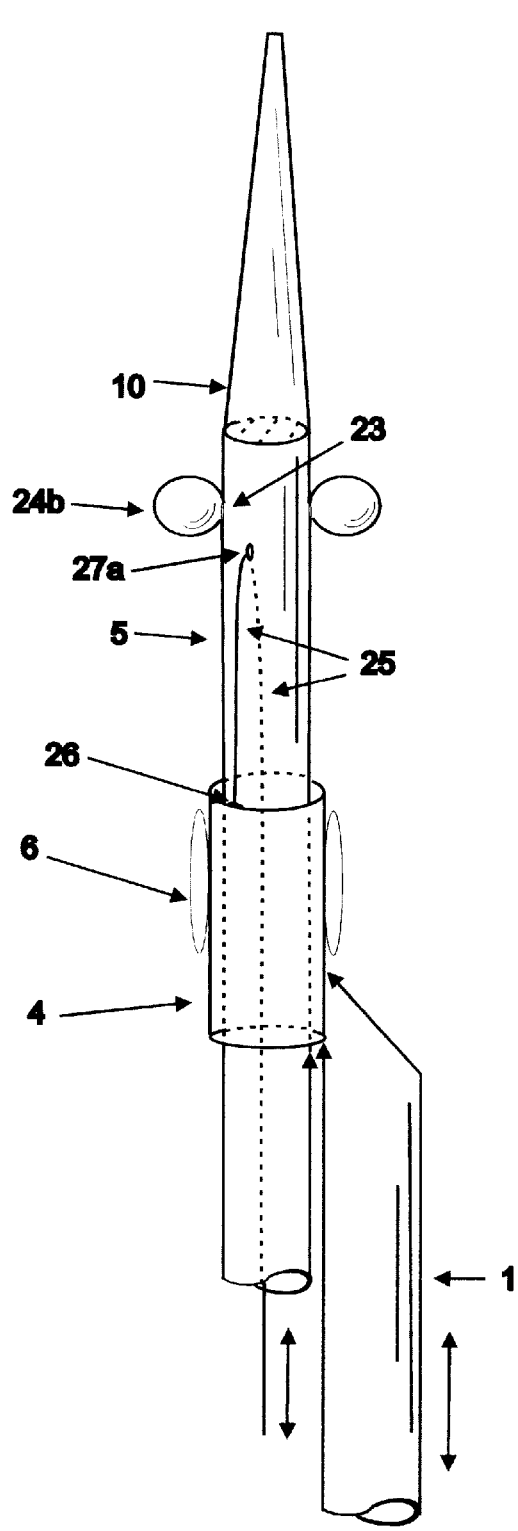

FIG. 8A is a perspective view of a hollow guidewire over which a monorail type catheter is both directly pushed by the operator and indirectly pulled by the operator pulling on a messenger wire that is inside the lumen of the hollow guidewire and that turns around a turning point formed by an aperture through the hollow guidewire at approximately its distal end and thence external to the guidewire through the orifice, proximally, to the distal end of the monorail catheter, to which the distal end of the wire is attached.

Figure 8B:
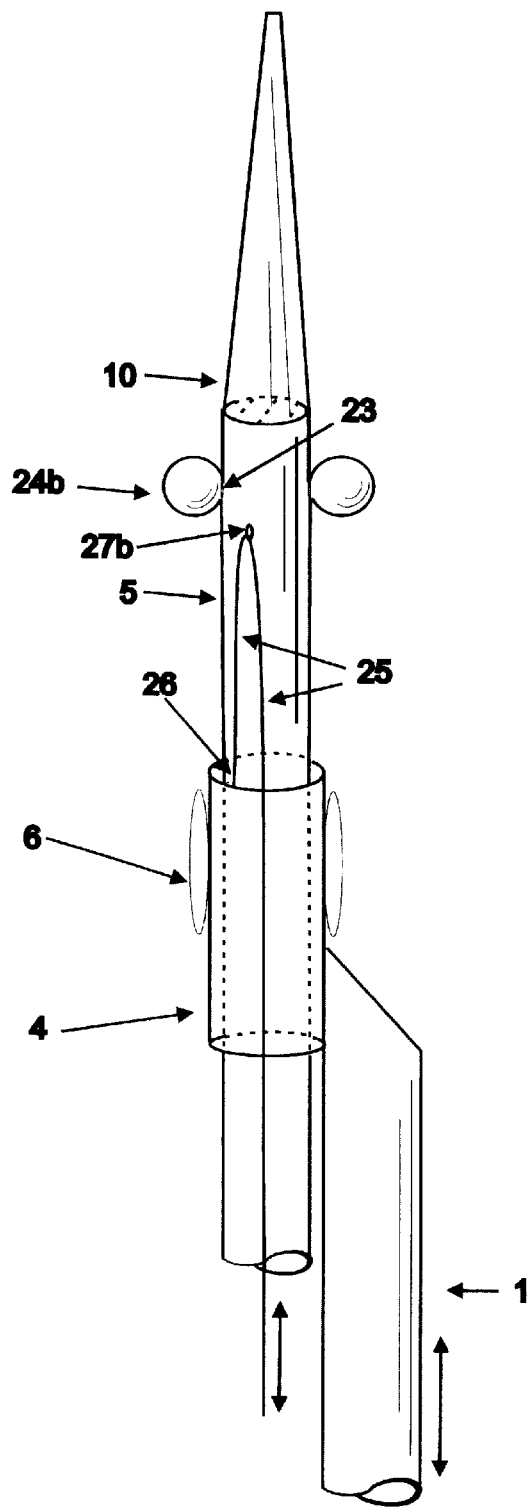

FIG. 8B is a perspective view of a hollow guidewire as illustrated in FIG. 4A above, except that the wire is external to the hollow guidewire and turns around a turning point wholly on the outside surface of the hollow guidewire.

Figure 9:
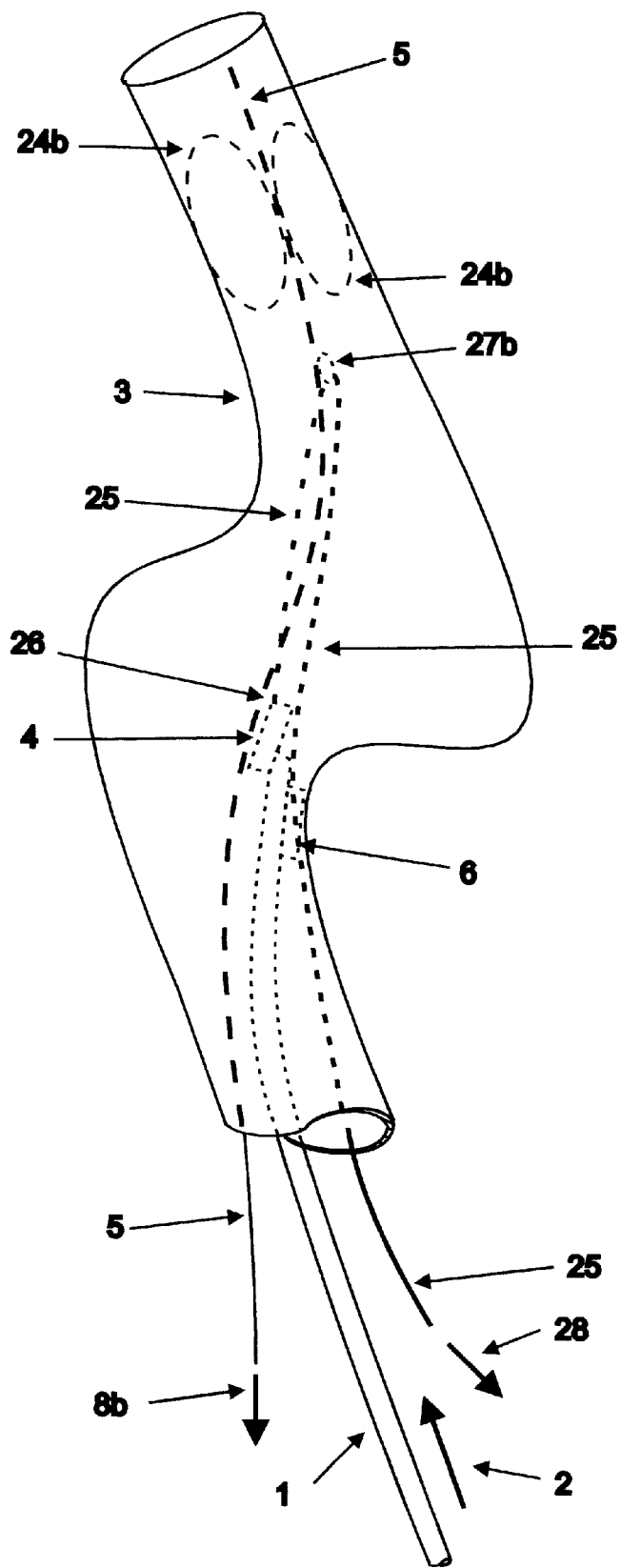

FIG. 9 is a perspective view of a body lumen containing the hollow guidewire that is held near its distal end against the inside walls of the body lumen, by an inflated cuff, and illustrates tension being applied to the guidewire at its proximal end by the operator pulling on the guidewire. The perspective view also illustrates the catheter being pushed by the operator and the messenger wire that is connected to the distal end of the catheter being pulled by the operator.

Figure 10:
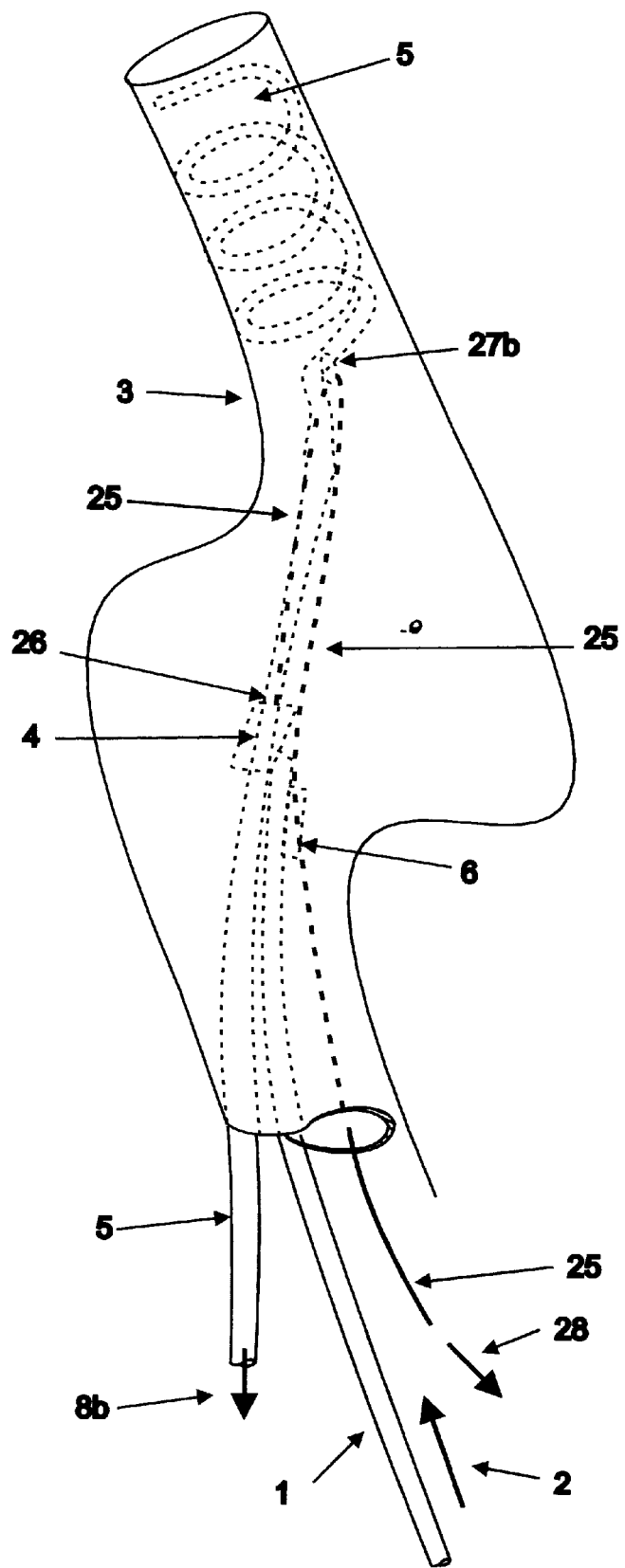

FIG. 10 is a perspective view of that device illustrated in FIG. 9, except that instead of an inflatable cuff or balloon, the hollow guidewire has been transformed into its memorized shape, in this case a coil that presses against the inside wails of the body lumen, holding the distal end of the guidewire in place.

Figure 11:
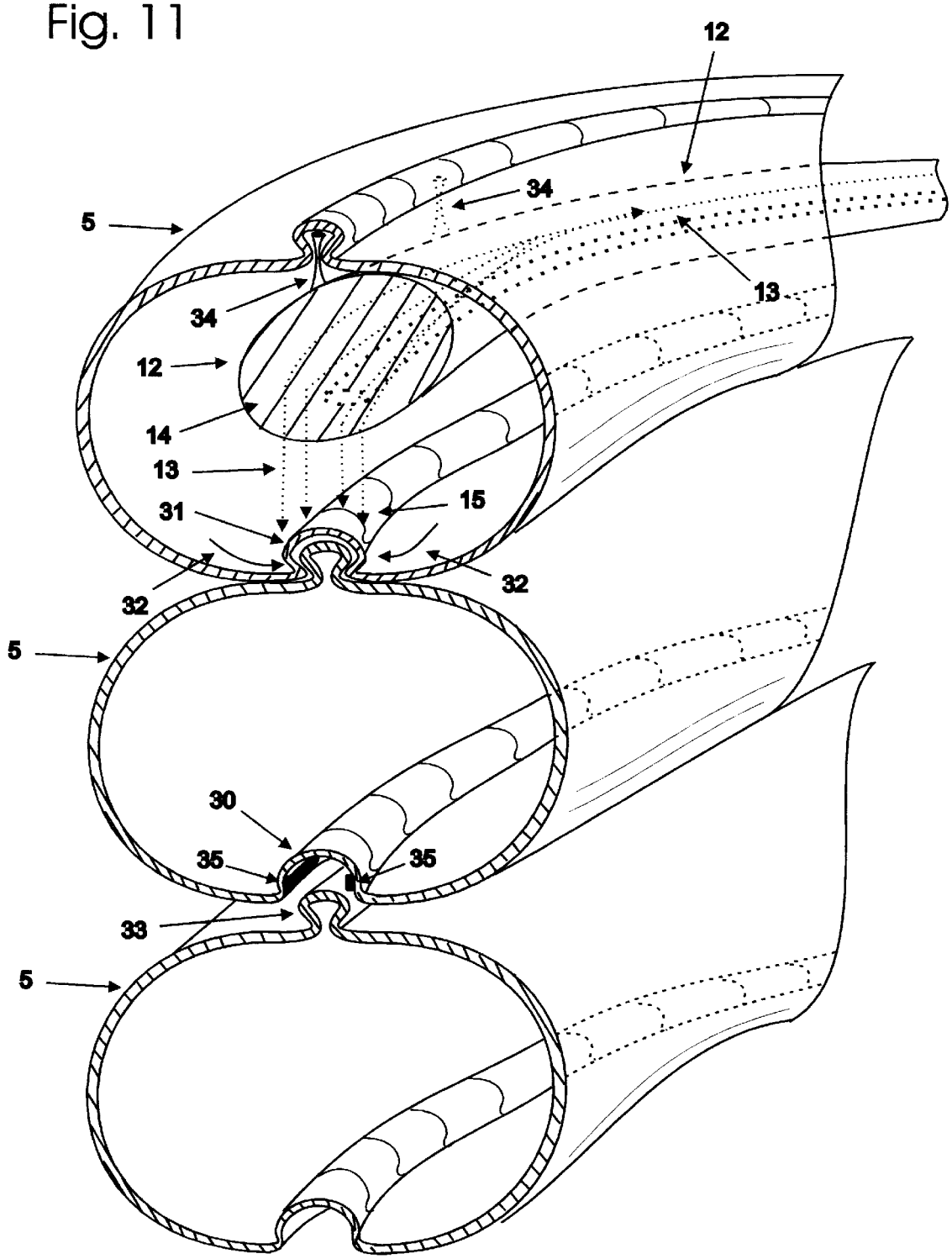

FIG. 11 is a perspective view of a coil that is formed from the guidewire transforming itself into its memorized shape in two steps. The first step being the general shape of a coil and the second or zipper step in which the coils are locked to together from one end to the other, forming a rigid tube.

FIG. 12 is a perspective view of a coil with its turns connected together by a coupling that is being unzipped by the application of a cooling material that relaxes one of the couples and causes the coupling to open, releasing the coils at that point. This FIG. 12 also shows the combination optical fiber and cooling tube.

FIG. 13 a detailed view of the distal end of the combination optical fiber and cooling tube with end-cap that redirects the cooling material approximately normal to the longitudinal axis of the optical fiber.

Figure 14:
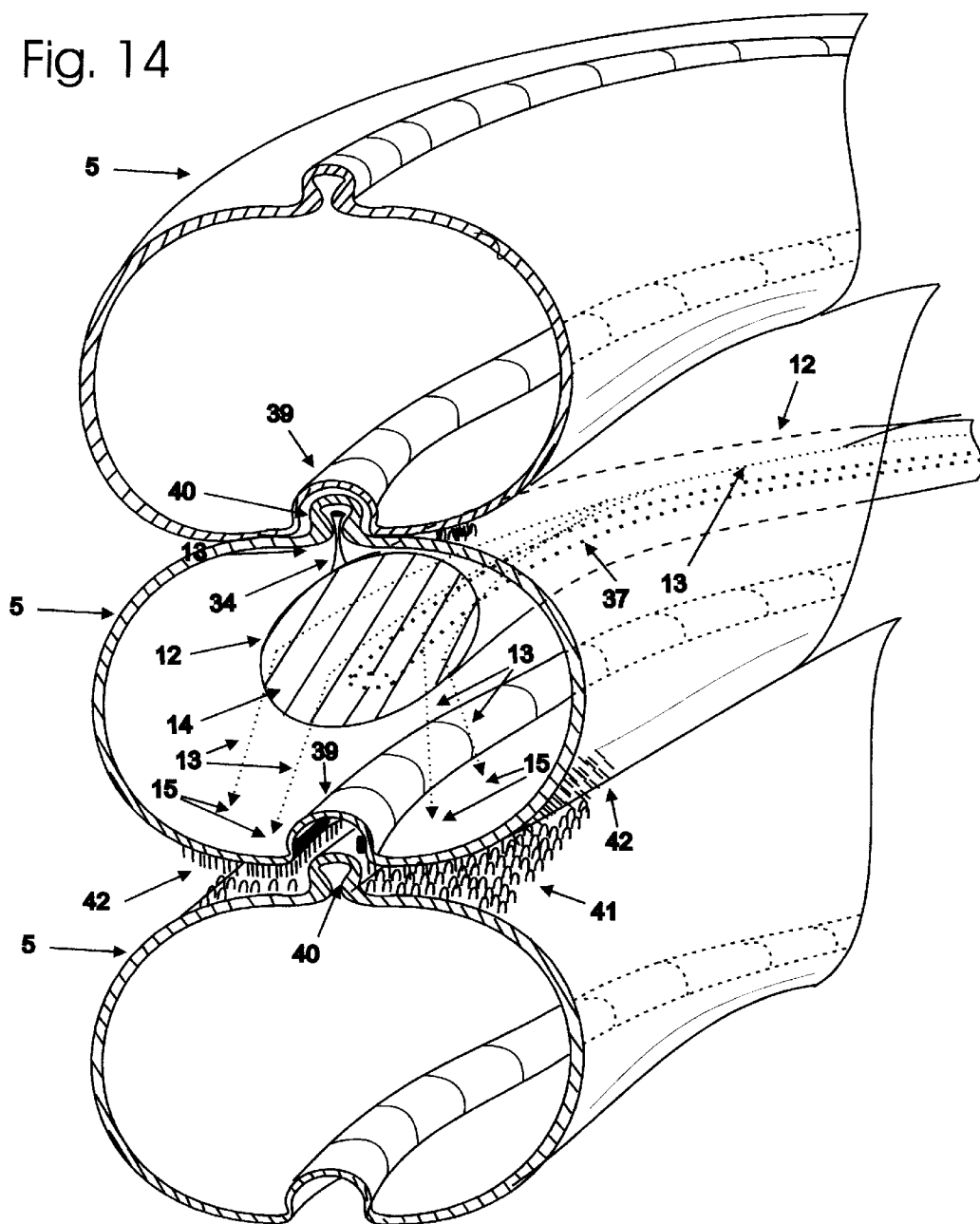

FIG. 14 is a perspective view of a coil that is formed from the guidewire transforming itself into its memorized shape in two steps. The first step being the general shape of a coil and the second or zipper step in which the coils are locked to together from one end to the other, by a controllable hooking finger and loop coupling device to form a rigid tube.

Figure 15:
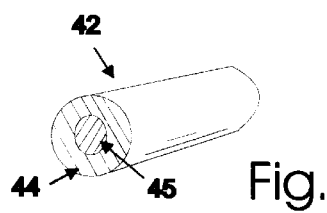

FIG. 15 is a perspective view of a hooking finger made of a combination of springing element and shape memory alloy element.

Figure 16A:
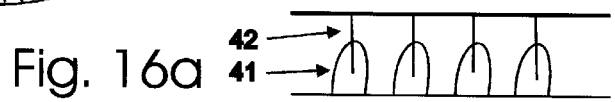
Figure 16B:
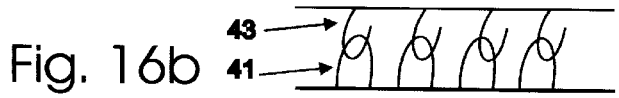

FIG. 16a and 16b illustrate the action of the hooking finger as it is disingaged in FIG. 16a and then becomes hooked, engaging the loops in FIG. 16b.

DESCRIPTION

FIG. 1A illustrates what happens when a monorail catheter 1 is pushed 2 by the operator into a lumen of a body cavity 3, its monorail receiver 4 sliding over the hollow guidewire 5. The monorail catheter in this case having a balloon 6 attached at approximately its distal end. The distal end of the monorail catheter, which is relatively stiff compared to the compliant guidewire, has a tendency to distort the guidewire and push it against the bend of the body orifice 7, preventing further passage of the monorail catheter. This can be compared to FIG. 1B where the hollow guidewire 5 has been pressurized, once in place. In this case the hollow guidewire becomes stiffer and straighter, thereby maintaining for the most part the hollow guidewire's smooth relatively large radius curves, and allowing the monorail catheter 1 to proceed around the bends of the said curvaceous body lumen. This effect can be achieved and enhanced if the hollow guidewire is put into tension between 8a and 8b, which also straightens it and increases the radius of curvature.

A preferred embodiment of the invention shown in FIG. 2A and 2B comprises as its main elements a hollow guidewire 5 that has a lumen that passes down a distance of the said guidewire. At the proximal end of the said guidewire 5 there is a means 9 of pressurizing the lumen of the said tube with a saline solution or other suitable material. This pressurizing means is well known to the art and includes a simple piston similar to that used to inflate angioplasty balloons. A compliant tippet 10 can be attached to the end of the hollow guidewire, but need not be. FIG. 2A and 2B are examples of the effect of varying the pressure of the lumen of the hollow guidewire when a force 11 is applied approximately normal to the longitudinal axis of the guidewire. In the first case, as illustrated in FIG. 2A, the hollow guidewire is not pressurized and the force 11 causes the tube adjacent to the point at which the force is applied, to bend. In the second case, as illustrated in FIG. 2B, the hollow guidewire is pressurized and the guidewire remains approximately straight and approximately unaffected by the application of the said force 11. Depending upon the shape of the hollow guidewire when it is not pressurized, the pressurized hollow guidewire can assume many different shapes at varying pressures. But in most cases the hollow guidewire will be fabricated to be straight in its relaxed state.

A preferred embodiment of the invention is illustrated on FIG. 3A, 3B and 3C that illustrate the hollow guidewire 5 that is made of shape memory effect or superelastic shape memory alloy, that has been first fed into a body lumen (not shown) and into which an optical fiber 12 is subsequently fed. The optical fiber delivers photo-thermal energy 13, from an external source to the distal end of the said optical fiber. At the distal end of the said fiber the photo-thermal energy is redirected by a redirecting means 14 onto the inner surface 15 of the hollow guidewire. The redirecting means can include a mirrored concave conical surface on the distal end of the said optical fiber, a mirrored beveled distal end or other similar redirecting means all well known to the art of fiber optics. The photo-optical energy can be delivered by many methods as taught by Unsworth and Waram in a copending patent application, Ser. No. 08/749661 filed on Nov. 15, 1996 to any part or parts of the interior of the said hollow guidewire to stiffen it where required and to shape it into practically any shape to better guide catheters that are subsequently slid along the said guide into the body lumen; the means illustrated on FIG. 3A, 3B and 3C being only an example of those methods.

Figure 4:
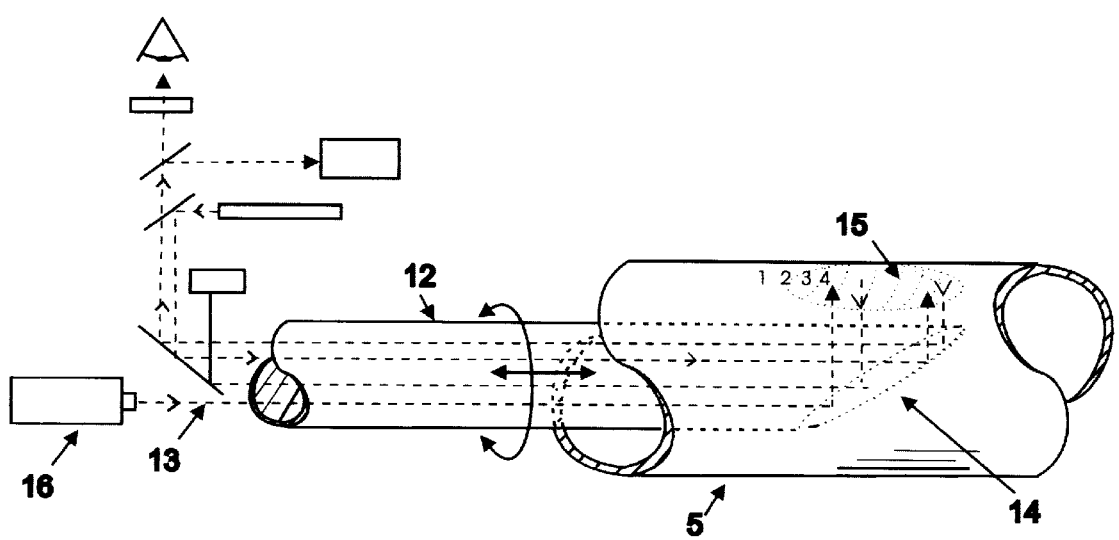
FIG. 4 is a perspective view of a device used in combination with a method taught by Unsworth and Waram in a copending patent application, Ser. No. 08/749661 filed on Nov. 15, 1996 for applying thermal energy to the inside of SMA tubes to recover parts of the shape that was fixed into them at high temperature.

FIG. 4 is included by way of reference and has been abstracted in part from the patent application of Unsworth and Waram in a copending patent application, Ser. No. 08/749661 filed on Nov. 15, 1996 to illustrate the more complete device used to apply photo-thermal energy to parts of the inside of a tube and in this case in the inside of the hollow guidewire. An external photo-thermal generator 16 has its photo-thermal energy 13 directed by an optical fiber 12 and then redirected by redirecting means 14 on the distal end of the optical fiber 12. Such redirected photo-thermal energy is then projected as a pattern on the inner surface 15 of guidewires. Means to monitor and control the application of the photo-thermal energy is also included.

The preferred embodiments that have their shape altered by the application of thermal energy, can also be altered by the application of cold saline or other fluid material pumped into the lumen or lumens of the guidewire, which temperature is either below that at which the material of the guidewire fully changes from austenite to martensite, that is, the martensite finish temperature, or which temperature is between the martensite start temperature and the martensite finish temperature, such that the material is only partially transformed to martensite from austenite. This cooling of the guidewire can be effected in combination with the thermal heating to vary the shape as required. Small patches of the inside of a shape memory effect tube or the guidewire in this example can be cooled, in an analogous way to that taught by Unsworth and Waram in a copending patent application, Ser. No. 08/749661 filed on Nov. 15, 1996. This heating and cooling could also be effected by a the use of a Peltier junction device attached for the end of a probe which would pass down the lumen of the shape memory tube.

FIG. 5 illustrates another means of effecting such cooling by inserting into the lumen of the tube or guidewire 5 a flexible delivery tube 17 with side-firing orifice 18 that delivers a spray 19 of a cooling material of various patterns onto the inside surface 20 of the tube or guidewire. Another means of delivering this cooling material is shown on FIG. 12. The cooling material is delivered it through a lumen 37 in the optical fiber 12 through a side-firing orifice 18 producing a spray 19 that is projected onto the inside surface 20 of the tube. A detailed perspective view is shown on FIG. 13 that illustrates the distal end of the combination optical fiber and cooling tube with end-cap 38 that contains a channel that redirects the flow of the cooling material approximately normal to the flow down the optical fiber 12. It should be noted that the end-cap 38 is not shown on FIG. 12 for diagrammatic clarity and that instead of an end-cap a lumen might be introduced normal to the longitudinal axis of the optical fiber such that it intersects with the lumen 37 some convenient distance proximal to the distal end of the optical fiber and the lumen 37 between this point of intersection and the distal end of the lumen is stopped-up. The mirrored surface 14 that redirects the photo-thermal energy that passes down the optical fiber, when heating is required, is also shown on FIG. 13. This combination heating and cooling means is thought to be the most convenient embodiment of the invention, as lumens can easily be fabricated into optical fibers and this permits much more precise control over the shaping of the shape memory alloy or superelastic material. While the preferred embodiment combines the means to deliver thermal-optical energy as well as cooling material to a particular part of the inside of the tube; one could just as easily deliver heating and cooling material down the lumen 37 to provide the heating and the cooling and thereby dispense with the laser and substitute the optical fiber for a simple tube 17 with side-firing distal end as illustrated in FIG. 5.

A preferred embodiment of the invention is to fabricate the hollow guidewire so that it is comprised of a tube 5a within a tube 5b as illustrated in FIG. 6A, or tube 5a within tubes 5b, 5c as illustrated in FIG. 6B, each bonded to the other mechanically or chemically, so that the tubes act as one element. Any number of tubes might be so configured.

FIGS. 6A, 6B, and 6C are cross-sectional views of three possible embodiments of the invention. Each tube can be made of shape memory alloy material or other material, and can be manufactured such that it is superelastic or has the shape memory effect. Each tube can have different shapes fixed in at high temperatures, have different temperatures at which they change phase from martensite to austenite and vise versa, have different thicknesses, different forces and other mechanical characteristics on recovery in the austenitic phase and in deformation in the martensitic phase.

For example while the two tubes are in their martensitic state, the outside tube can be stretched radially or longitudinally, or both; the inside tube being shrunk radially or longitudinally, or both. One tube would then be inserted into the lumen of the other, so that they are press-fit together facilitated by springback, that results from the elastic response of the tubes while in their martensitic phase. When one or both of the tubes are then transformed into their austenitic phase, the composite tube (as opposed to the single tubes) will stiffen due to an induced longitudinal tension in one of the tubes in combination with longitudinal compression in the other tube.

As demonstrated in FIG. 6C, holes 21 or openings of various shapes and sizes, can make accessible tubes otherwise separated from the lumen of the assemblage, by intermediate tubes. Openings through these intermediate tubes allow for the photo-thermal energy to be projected directly on these outside tubes 22. By varying the characteristics of the photo-thermal energy that is projected onto the inside surfaces of the hollow guidewire, including the duration, area and intensity, one can create many different shapes and stiffnesses along the hollow guidewire. The layered tubes also permit shapes to be recovered in one layer, and then another shape can be recovered and effectively erase the first shape, when the second layer is heated above its austenite finish temperature, and the second layer exerts a greater force than the first. Such an assemblage can form part or be the whole of any device and is not restricted to being applied as a guidewire but may be applied to any assemblage requiring modification of shape. Similarly cooling means like those given by way of example above can cool these surfaces to impart further control on the shaping of the tube.

While these layered tubes with or without holes, are given as examples of the invention of a hollow guidewire system, it is to be understood that such configurations may form parts of different devices that take advantage of the characteristics imparted by such arrangements in combination with heating and cooling means to change the shape and physical nature of the various layers.

The preferred embodiment of the invention shown in FIG. 7A and 7B comprises as its main elements a hollow guidewire 5 that has a lumen that passes down a distance of the said tube to approximately its distal end. As in the immediately preceding preferred embodiment, a saline solution or other material can be pressurized and depressurized in the lumen of the said hollow guidewire by well known pressurizing and depressurizing means 9. Near the distal end of the said hollow guidewire 5, there is at least one aperture 23 through which the pressurized fluid in the lumen of the said guidewire 5, passes into at least one balloon 24a on FIG. 7A and 24b on FIG. 7B. When the said fluid is not pressurized or a vacuum created, the balloon is deflated 24a as shown on FIG. 7A and when the said fluid is pressurized, the balloon is inflated 24b as shown on FIG. 7B. The compliant tip 10 can be attached to the end of the hollow guidewire, but need not be. The said balloon 24b is of sufficient size that when inflated it presses against the inside wall of the lumen of the body cavity, with sufficient force to immobilize the balloon relative to the point of contact with the said lumen of the body cavity. If one or more balloons are used, they may be sized such that there remain gaps through which the blood or other body fluids can continue to flow.

The preferred embodiment of the invention shown in FIG. 8A and 8B comprises as its main elements a hollow guidewire 5 that has a lumen that passes down a distance of the said tube. FIG. 8A and 8B have balloons 24b attached to the said hollow guidewire 5 that are inflated and deflated for the same purposes as described in the immediately preceding preferred embodiment. FIG. 8A and 8B illustrate a monorail catheter 1 with monorail receiver 4 and attached balloon 6 being pulled along hollow guidewire 5 by the messenger wire 25, which is attached at one end 26 to the said catheter 1. The messenger wire 25 then passes through an aperture 27a as shown in FIG. 8A and thence down through the lumen of the said hollow guidewire 5 to a point at which it can be pulled by the operator. Alternatively, the messenger wire 25 can pass through a tuning point such as a loop, pulley, slider or ring 27b as shown in FIG. 8B, in which case the messenger wire passes down external to the hollow guidewire 5 to a point at which it can be pulled by the operator. When the messenger wire is pulled by the operator the catheter 1 and attached balloon 6 or other device, are pulled in the direction of the distal end of the hollow guidewire. The messenger wire 25 is usually pulled in combination with the operator pushing the catheter 1 to effect the purpose of advancing or withdrawing the device 6 in the lumen of the body cavity. While FIG. 8A and 8B illustrate a device including balloons 24b, these may not be needed, for example, if the hollow guidewire is sufficiently rigid that it does not collapse when the messenger wire 25 is pulled by the operator. In the last example, the hollow guidewire might, if not sufficiently rigid, collapse between the point of attachment 26 to the catheter 1 and the aperture 27a when the messenger wire is pulled by the operator.

A preferred embodiment of the invention is illustrated on FIG. 9 showing the hollow guidewire 5 after placement in the lumen of the body cavity 3 and after the balloon or balloons 24b have been inflated to hold the approximately distal end of the hollow guidewire 5 in place against the walls of the said body cavity. The proximal end of the hollow guidewire 5 can be pulled 8b by the operator, putting the hollow guidewire into tension and thereby straightening the guidewire, increasing the radius of the guidewire's bends and resisting the forces normal to the longitudinal axis of the guidewire 5 imposed by the monorail catheter 1 being pushed 2 by the operator, as more particularly described above. The proximal end of the messenger wire 25 can also be pulled 28 to counteract the effects of pushing on the monorail catheter 1 described above and illustrated on FIG. 1A.

A preferred embodiment is illustrated on FIG. 10 which illustrates another method of anchoring the distal end of the guidewire against the inside walls of the body lumen. Rather than an anchoring balloon, the hollow guidewire is made of shape memory alloy that has a shape set into the distal end of the tube at high temperature. This shape, which can be for example a coil, is then recovered when the distal end of the said hollow tube is heated sufficiently so that it changes from martensite to austenite. The means of heating includes those described above utilizing a side-firing laser. The advantage of this system is that blood flow is virtually uninterrupted by the small profile coil, when it is deployed. The part of the hollow guidewire that is required to recover as described above, is made of shape memory alloy. The other part of the guidewire could be superelastic material. Thus the hollow guidewire could be made of two sections: the primary section of superelastic material and the secondary part that is to have the shape recovered for the purposes of creating an anchor made of shape memory alloy. A springing element can be added to allow for the return of the guidewire to its straight shape from the memorized coil shape once the memorized shape has been cooled below its martensitic start temperature and becomes compliant, then assuming the straight shape of the coupled springing element. This springing element 44 can form a sheaf around the shape memory alloy element 45 as illustrated on FIG. 15 but could also be attached or coupled in many other ways.

Another preferred embodiment is shown on FIG. 11 which illustrates a means for zippering the adjoining turns of a coil together to form a rigid tube. This tube could be used for the anchor in some specialized cases and be unzipped to assist in withdrawing the device. What is meant by zippering is not simply holding two items together, but it includes gathering and positioning for assembly, and only then connecting them together. The zippered coil structure is made from shape memory alloy and is recovered into its final shape in two steps. The first step involves recovering the gross shape of the coil as described in the immediately preceding paragraph, with the exception that a strip along the inner surface is of guidewire 5 coincident with a couple 30 is not heated and thus is not recovered until the coil is formed. Once the gross shape of the coil is recovered, a second step of heating that part of the tube that was not heated in the first step, will cause the couple shape to recover from the martensitic shape of couple 30 to the austenitic recovered shape of couple 31 that will grip by pinching action 32 the complementary couple shape 33 on the next turn of the coil. An example of means to selectively heat the inside of the tube that forms the coil is shown on FIG. 11 as an optical fiber 12 that directs photo-thermal energy 13 down the said fiber from an external power source. The said photo-thermal energy is redirected by a mirror 14 or similar optical means for redirection well known to the art and known as side-firing optics, to project the said photo-thermal energy onto that part of the inner surface 15 of guidewire 5. The optical fiber can be positioned by a number of methods to ensure that the photo-thermal energy is directed to only that strip 30 that was not heated during the said step one of the procedure. FIG. 11 illustrates the optical fiber being positioned by one such means, that is by a hanger 34 which rides along the inside of the coupling 33. As can readily be appreciated, once any part of two adjacent coils are coupled together, the arrangement will behave like a zipper if the photo-thermal energy is directed along a path coincident with the inside of the tube 5 that forms the couple 30. The mating surfaces of the couples that form the coupling can include a sealant material 35 that will ensure a complete seal when the turns of the coil are completely coupled. While FIG. 11 illustrates the female couple having its shape recovered, there is no reason why the male couple could not be recovered to a larger size to effect the same purpose. The couples 30 and 33 of the tube 5 shown on FIG. 11 are an integral part of the tube 5, but the couples could also be attached to the said tube and not be an integral part of it. While this preferred embodiment is used to anchor the hollow guidewire to the inside of the body lumen, this method of creating larger tubes from smaller tubes could be used to line any body lumens including pipes, fabricate stents, assemble structures of any size and shape or fabricate heat exchangers in situ. It is also important to note that this method can be used to create a zipper out of two tubes, and the second step of the method above described. The tubes would normally be attached to objects that one would wish to connect. If used as a zipper, the zipper could be released by cooling the couple 30 below its martensitic start temperature, as illustrated in FIG. 12 in which case the couple would change shape from its pinched shape, as in couple 31, to its larger shape, as in couple 30. The tube 5 having been sprung by the pinching forces 32 on FIG. 11 when the couple 30 was heated and pinched into its pinched shape 31 would rebound 36 as illustrated on FIG. 12 and provide the force to restore the couple to its larger shape 30. Once in its larger shape, the two sections would be free to separate. FIG. 12 illustrates a preferred embodiment to provide the cooling of the couple. The means illustrated is comprised of a lumen 37 passing down the interior of the optical fiber 12 approximately parallel to the optical fiber's longitudinal axis. FIG. 13 illustrates a detailed perspective view of the distal end of the said optical fiber 12. The distal end of the optical fiber 12 has a end-cap 38 attached to it that redirects the flow of the cooling material approximately normal to the longitudinal axis of the optical fiber through an orifice 18 producing a stream or spray 19 that is projected onto a small region of inside surface 20 on the couple 30. Of course the same result could be effected by using similar means to change the shape of the male part of the coupling 33 in combination with changes in the female part of the coupling 30 to attach and reattach the tubes. Also the couple that does not have its shape altered need not be on the same continuous tube, but could be on any other object, allowing a tube containing the couple that does have its shape changed, to be attached zipper like, to any other object that has attached to it a couple of suitable and complementary shape. Another embodiment of the invention would place the heat and cooling source within the couple itself. In the case of the combination optical fiber and cooling tube described above, the longitudinal axis of the optical fiber and that of the couple would be parallel and the optical fiber would be drawn or pushed thought the cavity formed by the couple. Placing the couple on the inside of the couple would be particularly useful where the items being zippered together are not tubes but other objects to which the couples are attached or of which they are an integral part. In most cases the couple will be closed, that is the coupling will be mated, when the couple that undergoes a thermal change is in its austenitic phase after the said closing. The reason for this is that the shape memory alloy is much more rigid in its austenitic phase. Of course there may be circumstances in which both couples will be heated to recover their memorized shape. In most cases the couple will be disengaged when the shape memory alloy couple is cooled to below its martensitic start temperature because rigidity is not required when the couple is disengaged. As mentioned above, a spring bias is often desired to return the easily deformable martensitic material to a shape that will allow the couple to disengage from its mating couple. As mentioned above, when the couple forms part of a tube, the tube itself can provide the biasing; if the couple is not part of a tube, additional spring biasing must be provided, which can take many forms all well known to the are, including springs, polymer materials and bifurcated assemblies. Another approach is to use multiple layers of shape memory alloy material, other materials, and can be manufactured such that it is superelastic or has the shape memory effect. Each layer can have different shapes fixed at a high temperatures, have different temperatures at which they change phase from martensite to austenite and vise versa, have different thicknesses, different forces and other mechanical characteristics on recovery in the austenitic phase and in deformation in the martensitic phase. For example a couple with multiple layers could be opened and closed by heating the couple to two different temperatures.

This means of zippering assemblies together is not limited to the clincher type of coupling described in the preceding preferred embodiment. One could also use a hook and loop coupling to zipper assemblies together. This has the advantage of being more compliant. As illustrated on FIG. 14, FIG. 16a and FIG. 16b this is accomplished by attaching loops 41 of any suitable material on one surface and hooking fingers (or rods) 42 on the other surface. As illustrated on FIG. 15 hooking fingers are fabricated from a member of shape memory alloy 45, that when below its martensitic start temperature, is forced into a straight shape along its longitudinal axis by a springing element 44. This springing element can for example be a part of the finger and an attached sheath 44 as illustrated on FIG. 15. It can be made of spring metal, polymer spring or superelastic material. When however the hooking finger is heated above its austenitic finish temperature, the shape memory alloy core 45 recovers its memorized shape of a hook with sufficient force that it overcomes the spring's tendency to return it to a straight finger and hooks around the loops 41 drawing the two surfaces together with significant force. The finger 42 then becomes a hook 43 as illustrated on FIG. 16a and 16 b. The remarkable thing is that when the two surfaces are zippered together they may be unzipped by simply cooling the hooking fingers 43 below their martensitic start temperature, at which temperature the core that is made of shape memory alloy 45 relaxes and the springing element 44 returns it to a straight shape and thereby releases the hooking fingers and the surface to which they are attached. The heating and cooling required can be provided by those means described above, or by any other convenient means. As illustrated in FIG. 14 photo-thermal energy 13 is delivered from a remote source down an optical fiber 12 to a mirrored surface 14 inclined at approximately 45° to the longitudinal axis of the optical fiber 12. This example of a side-firing optical fiber projects the photo-thermal energy 13 onto the inside surface of the tube 5 at on the inner surface 15. The optical fiber is directed such that the hooking fingers 42 are raised to a sufficient temperature to recover their memorized shape and that the heating process is moved along the tube 5 in such a manner that there is a moving front of recovered hooking fingers 43 so that the system behaves like a zipper. FIG. 14 illustrates the particular use for such a system, to hold together the turns of a tube 5. Guides 39 and 40 are linear mating grooves in the tubes, parallel to the longitudinal axis of the tube, that assist in holding the turns of the tube in position prior to the engagement of the hooking fingers 42 and hoops 41. It should be noted that the springing element might just as easily act to turn the hooking finger 42 into a hook and the shape memory alloy part of the finger 45 form a straight rod when above its austenitic finish temperature. This reversed arrangement would act in a similar fashion to the first described system. It should also be noted that the springing element 44 need not form a sheaf around the shape memory alloy element 45, but could be bar shaped attached to a bar shaped shape memory alloy element. As can be readily appreciated the hooking finger acts like a finger that articulates in response to heating and cooling; contracting when heated, straightening when cooled or vise versa. Each hooking finger could of course have its own peltier junction that would heat and cool each hooking finger separately. Each hooking finger can be controlled by a separate microelectronic switch and their motion can be integrated and coordinated by a microelectronic controller, by methods well known to the art. Such an array of separately controllable hooking or articulating fingers can be attached to the sides of the guidewire to cause it to move centipede like down the body lumen.

Fortunately when the hooking fingers recover their shape, they do not immediately recover in their entirety, but rather gradually from the end that is proximal to the heat source to the end distal to the heat source. This allows for a gradual impulse rather than a flicking action. For example, the tube could be moved in two directions if one-half of the articulating fingers are all lined-up so they when they are relaxed they are straight and at a 30° angle to the longitudinal axis of the tube, and all pointing in the same direction, that being the first direction of travel and the other half are pointed in the opposite direction, being the second direction of travel and they are arranged in rows so that the motion of the first half does not interfere with the motion of the second half; and each articulating finger recovers from the initial said 30° angle and curls along a plane normal to the longitudinal axis of the tube that is coincident with the distal end and proximal end of the said articulating finger, at the initial position, so that the distal end passes through the position normal to the longitudinal axis of the said tube. If one wishes to move the tube in the first direction of travel, one would first recover all of the articulating fingers in the second group (these need not be used to travel in the first direction of travel, but would be used for travelling in the second direction of travel). The next step would be to recover one half or "A" group of the articulating fingers in the first group. This would move the tube in the first direction of travel. The next step would be to recover the other half of the first group or "B" group to the point where the distal ends of the articulating fingers were at a point most distant from the surface of the tube in a direction normal from the surface of the tube, the "apex" point. At this point recovery of "B" group would be turned off, and "A" group would be fully relaxed. "B" group would then be fully recovered. At this point the sequence would begin anew with "A" group being partly recovered to the apex point. As can be seen, the shape that is memorized in at high temperature must be such that when one group of articulating fingers is at its apex point, the others can be relaxed without touching the surface along which the tube is passing. As can be readily seen this method of locomotion would have many applications beyond directing a guidewire through a body lumen, the fingers themselves could be used for robotics or sign displays to name a few. In the case of the guidewire the articulating fingers could be used to assist in maneuvering the guidewire down the body lumen, tensioning the guidewire and then also acting as a hooking finger 43 as shown on FIG. 14 to zipper the turns of the tube 5 to form a larger tube.

While heating and cooling means have been referred to in this patent disclosure, it is to be understood that they are examples only and that any heating and cooling means can be applied to the hollow guidewires, the various layers of tubes forming the said hollow guidewires and other structures referred to herein; and while examples of heating means are generally from the inside of the assembly, the assemblies might also be heated from the outside using similar means.

While the present invention refers to shape memory alloy tubes or simply SMA tubes, it is to be understood that the invention includes tubes made of other materials that exhibit shape recovery when heated to an appropriate temperature. The references to shape memory alloy should then be considered to be by way of example only of a larger class of materials that exhibit similar properties. It should also be understood that term "wire" does not just refer to metal tubes, but tubes made of plastic or composites, and the term "guidewire" should be given a similar interpretation.

It should also be understood that while the description of the invention referred to in this disclosure gives examples of the guide system being used in operations on the human body, the system can be applied to any body or object that contains passages through which one would wish to insert a device. Body is intended to be interpreted in its broadest sense.

It should be understood that while the examples of tubes referred to in this disclosure and in the drawings are cylindrical, it is to be understood that tubes having a cylindrical cross-section are only examples of a larger class of tubes having many different cross-sections, for example, elliptical, triangular, square or star-shaped or combination thereof. It should also be understood that the tubes may have different wall thicknesses, or be tapered.

It should also be understood that while the hollow guidewire is shown with only one lumen, a plurality of lumens could be used, also separate lumens could be used to pressurize and depressurize the balloons and a separate lumen might accommodate the messenger wire. Also, separate tubes could be used for the various separate functions described in the invention; and one or more lumens could have open distal ends that would deliver materials to the body lumen. If a plurality of lumens is used, each might be pressurized independently at different pressures to change the shape of the hollow guidewire.

While the present invention has been described in conjunction with preferred embodiments, it is to be understood that modifications and variations may be resorted to without departing from the spirit and scope of the invention as those skilled in the art will readily understand. Such modifications and variations are considered to be within the purview and scope of the inventions and appended claims.

What is claimed is:

1. A system for guiding devices or materials into body lumens, comprising:
   a guidewire having a proximal end, a distal end spaced from the proximal end, and one or more lumens extending through the guidewire from the proximal end to approximately the distal end, wherein said guidewire is comprised of a shape memory alloy (SMA) or other shape memory material and has a memorized shape which is relaxed by the extraction of thermal energy and is at least partly recovered with the application of thermal energy;
   heating means adapted for selective, localized heating of said guidewire to thereby straighten and stiffen all or part of said guidewire; and
   a catheter or device, that is slidably attached to said guidewire, and that is adapted to be slid along said guidewire into a body lumens; and wherein said heating means comprises an optical fiber extending through one of the lumens of the guidewire, said optical fiber having a proximal end and a distal end, said optical fiber being adapted to deliver photo-thermal energy along the optical fiber.

2. The system of claim 1, wherein the distal end of the optical fiber is provided with redirecting means which re-direct and project said photo-thermal onto an inner surface of said lumen of the guidewire.

3. The system of claim 1, wherein said optical fiber further has a lumen extending from said proximal end to said distal end of said optical fiber, said lumen of said optical fiber being adapted to deliver heating or cooling fluids or both from the proximal end to the distal end of the optical fiber.

4. The system of claim 3, wherein said optical fiber includes means for redirecting flow of said fluids normal to a longitudinal axis of said optical fiber.

5. The system of claim 1, wherein the guidewire is made of a shape memory alloy (SMA) material that is deformable from a previously memorized shape in a deformation state selected from one or more of bending, tension and torsion, and at a temperature at or above an austenite finish temperature of the SMA material such that the SMA material exhibits superelastic behavior by forming stress-induced martensite or exhibits pure elastic behavior, or some combination of both superelastic and elastic behavior in different areas or layers of the guidewire, and wherein the application of thermal energy causes the SMA material to increase in temperature, which causes the stiffness of the guidewire to increase and thereby attempt to resume its memorized shape either by a concomitant increase in elastic modulus of the SMA material or by an increase in a value of a superelastic stress plateau, which is a stress at which the stress-induced martensite is first formed, or by a combination thereof, or other more complex deformation and recovery paths occurring as a function of stress, strain and temperature, including complex subloops at temperatures at or above the austenite finish temperature of the SMA material.

6. The system of claim 5, wherein the SMA material is a nickel/titanium alloy.

7. A system for guiding devices or materials into body lumens, comprising:
   a guidewire having a proximal end, a distal end spaced from the proximal end, and one or more lumens extending through the guidewire from the proximal end to approximately the distal end, wherein said guidewire is comprised of an inner tube enclosed within an outer tube along at least a part of its length, each of the inner tube and the outer tube comprising a shape memory alloy (SMA) or other shape memory material and having a memorized shape which is relaxed by the extraction of thermal energy and is at least partly recovered with the application of thermal energy wherein, during shape recovery, one of said tubes is in compression parallel to its longitudinal axis and the other of said tubes is in tension parallel to its longitudinal axis;
   heating means adapted for selective, localized heating of said guidewire to thereby change the shape, the radii of its curves and the rigidity of all or part of said guidewire; and
   a catheter or device, that is slidably attached to said guidewire, and that is adapted to be slid along said guidewire into a body lumens.

8. The system of claim 7, wherein said heating means comprises an optical fiber extending through one of the lumens of the guidewire, said optical fiber having a proximal end and a distal end, said optical fiber being adapted to deliver photo-thermal energy along the optical fiber.

9. The system of claim 8, wherein the distal end of the optical fiber is provided with redirecting means which re-direct and project said photo-thermal energy onto an inner surface of said lumen of the guidewire.

10. The system of claim 8, wherein said optical fiber further has a lumen extending from said proximal end to said distal end of said optical fiber, said lumen of said optical fiber being adapted to deliver heating or cooling fluids or both from the proximal end to the distal end of the optical fiber.

11. The system of claim 10, wherein said optical fiber includes means for redirecting flow of said fluids normal to a longitudinal axis of said optical fiber.

12. The system of claim 7, wherein the guidewire is deformable from a previously memorized shape in a deformation state selected from one or more of bending, tension and torsion, and at a temperature at or above an austenite finish temperature of the SMA material such that the SMA material exhibits superelastic behavior by forming stress-induced martensite or exhibits pure elastic behavior, or some combination of both superelastic and elastic behavior in different areas or layers of the guidewire, and wherein the application of thermal energy causes the SMA material to increase in temperature, which causes the stiffness of the guidewire to increase and thereby attempt to resume its memorized shape either by a concomitant increase in elastic modulus of the SMA material or by an increase in a value of a superelastic stress plateau, which is a stress at which the stress-induced martensite is first formed, or by a combination thereof, or other more complex deformation and recovery paths occurring as a function of stress, strain and temperature, including complex subloops at temperatures at or above the austenite finish temperature of the SMA material.

13. The system of claim 12, wherein the SMA material is a nickel/titanium alloy.

14. A system for guiding devices or materials into body lumens, comprising:

a guidewire having a proximal end, a distal end spaced from the proximal end, and one or more lumens extending through the guidewire from the proximal end to approximately the distal end, wherein said guidewire is comprised of an inner tube enclosed within an outer tube along at least a part of its length, each of the inner tube and the outer tube comprising a shape memory alloy (SMA) or other shape memory material and having a memorized shape which is relaxed by the extraction of thermal energy and is at least partly recovered with the application of thermal energy wherein, during shape recovery, one of said tubes is in compression radially, normal to its longitudinal axis, and the other of said tubes is in tension radially, normal to its longitudinal axis;

heating means adapted for selective, localized heating of said guidewire to thereby change the shape, the radii of its curves and the rigidity of all or part of said guidewire; and a catheter or device, that is slidably attached to said guidewire, and that is adapted to be slid along said guidewire into a body lumens.

15. The system of claim 14, wherein said heating means comprises an optical fiber extending through one of the lumens of the guidewire, said optical fiber having a proximal end and a distal end, said optical fiber being adapted to deliver photo-thermal energy along the optical fiber.

16. The system of claim 15, wherein the distal end of the optical fiber is provided with redirecting means which re-direct and project said photo-thermal energy onto an inner surface of said lumen of the guidewire.

17. The system of claim 15, wherein said optical fiber further has a lumen extending from said proximal end to said distal end of said optical fiber, said lumen of said optical fiber being adapted to deliver heating or cooling fluids or both from the proximal end to the distal end of the optical fiber.

18. The system of claim 17, wherein said optical fiber includes means for redirecting flow of said fluids normal to a longitudinal axis of said optical fiber.

19. The system of claim 14, wherein the guidewire is deformable from a previously memorized shape in a deformation state selected from one or more of bending, tension and torsion, and at a temperature at or above an austenite finish temperature of the SMA material such that the SMA material exhibits superelastic behavior by forming stress-induced martensite or exhibits pure elastic behavior, or some combination of both superelastic and elastic behavior in different areas or layers of the guidewire, and wherein the application of thermal energy causes the SMA material to increase in temperature, which causes the stiffness of the guidewire to increase and thereby attempt to resume its memorized shape either by a concomitant increase in elastic modulus of the SMA material or by an increase in a value of a superelastic stress plateau, which is a stress at which the stress-induced martensite is first formed, or by a combination thereof, or other more complex deformation and recovery paths occurring as a function of stress, strain and temperature, including complex subloops at temperatures at or above the austenite finish temperature of the SMA material.

20. The system of claim 19, wherein the SMA material is a nickel/titanium alloy.

* * * * *